(12) United States Patent
Frietze

(10) Patent No.: US 6,294,671 B1
(45) Date of Patent: Sep. 25, 2001

(54) ISOXAZOLO[4, 5-D]PYRIMIDINES AS CRF ANTAGONISTS

(75) Inventor: William Eric Frietze, Kennett Square, PA (US)

(73) Assignee: DuPont Pharmaceuticals Company, Wilmington, DE (US)

(*) Notice: Subject to any disclaimer, the term of this patent is extended or adjusted under 35 U.S.C. 154(b) by 0 days.

(21) Appl. No.: 09/379,143

(22) Filed: Aug. 20, 1999

Related U.S. Application Data

(60) Provisional application No. 60/097,386, filed on Aug. 21, 1998.

(51) Int. Cl.$^7$ .................... C07D 487/04; A61K 31/519; A61P 25/24
(52) U.S. Cl. ............................ 544/276; 544/278
(58) Field of Search .................... 544/278, 276

(56) References Cited

FOREIGN PATENT DOCUMENTS

| | | | |
|---|---|---|---|
| 0778277 | * | 6/1997 | (EP) . |
| 0778277 | | 6/1999 | (EP) . |
| 9519774 | | 7/1995 | (WO) . |
| 9808847 | * | 3/1998 | (WO) . |

OTHER PUBLICATIONS

Desimoni et al. Tetrahedron 23, 675–680, 1967.*
Laurent et al. Bull. Soc. Chim. BeLg. 103(5–6) 181–184, 1994.*
Swerdlow, N.R. et al., Corticotropin–Releasing Factor Potentiates Acoustic Startle in Rats: Blockade by Chlordiazepoxide, Psychopharmacology, 1986, pp. 147–152.
Berridge, C.W. and Dunn, A.J., Corticotropin–Releasing Factor Elicits Naloxone Sensitive Stress–Like Alterations in Exploratory Behavior in Mice, Regulatory Peptides, 1986, pp. 83–93.
Britton, K.T. et al., Chlordiazepoxide Attenuates Response Suppression Induced by Corticotropin–Releasing Factor in the Conflict Test, Psychopharmacology, 1985, pp. 170–174.
Grigoriadis et al., Effects of Chronic Antidepressant and Benzodiazepine Treatment on Corticotropin–Releasing–Factor Receptors in Rat Brain and Pituitary, Neuropsychopharmacology, 1989, pp. 53–60.
France, R.D. et al., CSF Corticotropin–Releasing–Factor–Like Immunoactivity in Chronic Pain Patients With and Without Major Depression, Biol. Psychiatry, 1988, pp. 86–88.
Vale, M. et al., Chemical and Biological Characterization of Corticotropin Releasing Factor, Recent Progress in Hormone Research, 1983, pp. 245–270.
Morley, J.E. et al., Neuropeptides: Conductors of the Immune Orchestra, Life Sciences, 1987, pp. 527–544.
Banki, C.M. et al., CSF Corticotropin–Releasing Factor–Like Immunoreactivity in Depression and Schizophrenia, Am. J. Psychiatry, 1987, pp. 873–877.

Nemeroff, C.B. et al., Elevated Concentrations of CSF Corticotropin–Releasing Factor–Like Immunoreactivity in Depressed Patients, Science, 1984, pp. 226–227.
Vale, M. et al., Characterization of a 41–Residue Ovine Hypothalamic Peptide That Stimulates Secretion of Corticotropin and Beta–Endorphin, Science, 1981, pp. 1394–1397.
Nemeroff, C.B. et al., Reduced Corticotropin Releasing Factor Binding Sites in the Frontal Cortex of Suicide Victims, Arch. Gen. Psychiatry, 1988, pp. 577–579.
Britton, K.T. et al., Intraventricular Corticotropin–Releasing Factor Enhances Behavioral Effects of Novelty, Life Sciences, 1982, pp. 363–367.
Koob, G.F. and Britton, K.T., Behavioral Effects of Corticotropin–Releasing Factor, Basic and Clinical Stuides of a Neuropeptide, 1990, pp. 253–265.
Britton, K.T. et al., Corticotropin Releasing Factor and Amphetamine Exaggerate Partial Agonist Properties of Benzodiazepine Antagonist Ro 15–1788 in the Conflict Test, Psychopharmacology, 1988, pp. 306–311.
Blalock, J. Edwin, A Molecular Basis for Bidirectional Communication Between the Immune and Neuroendocrine Systems, Physiological Reviews, 1989, pp. 1–32.
Berridge, C.W. and Dunn, A.J., A Corticotropin–Releasing Factor Antagonist Reverses the Stress–Induced Changes of Exploratory Behavior in Mice, Hormones and Behavior, 1987, pp. 393–401.
De Souza, E.B. et al., Corticotropin–Releasing Factor Receptors are Widely Distributed Within the Rat Central Nervous System: An Autoradiographic Study, The Journal of Neuroscience, 1985, pp. 3189–3203.
Gold, P.W. et al., Psychiatric Implications of Basic and Clinical Studies With Corticotropin–Releasing Factor, The American Journal of Psychiatry, 1984, pp. 619–627.
De Souza, E.B., CRH Defects in Alzheimer's and Other Neurologic Diseases, Hospital Practice, 1988, pp. 59–71.

(List continued on next page.)

Primary Examiner—Richard L. Raymond
Assistant Examiner—Venkataraman Balasubramanian
(74) Attorney, Agent, or Firm—Kenneth B. Rubin; Kalim S. Fuzail

(57) ABSTRACT

The present invention describes novel isoxazolo[1,5-a]pyrimidines of formula:

I

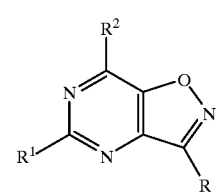

wherein R is an aromatic or heteroaromatic ring, or pharmaceutically acceptable salt form thereof, which are useful as CRF antagonists.

13 Claims, No Drawings

OTHER PUBLICATIONS

Arato, M. et al., Elevated CSF CRF in Suicide Victims, Biol. Psychiatry, 1989, pp. 355–359.

Holsboer, F. et al., ACTH and Multisteroid Responses to Corticotropin–Releasing Factor in Depressive Illness: Relationship to Multisteroid Responses After ACTH Stimulation and Dexamethasone Suppression, Psychoneuroendocrinology, 1984, pp. 147–160.

Berridge, C.W. and Dunn, A.J., Physiological and Behavioral Responses to Corticotropin–Releasing Factor Administration: Is CRF a Mediator of Anxiety or Stress Responses?, Brain Research Reviews, 1990, pp. 71–100.

Sapolsky, Robert M., Hypercortisolism Socially Subordinate Wild Baboons Originates at the CNS Level, Arch Gen Psychiatry, 1989, pp. 1047–1051.

Koob, George F., Strss, Corticotropin–Releasing Factor, and Behavior, Perspectives on Behaviroal Medicine, 1985, pp. 39–52.

River et al., Characterization of Rat Hypothalamic Corticotropin–Releasing Factor, Proc Natl Acad Sci, 1983, pp. 4851–4855.

* cited by examiner

ISOXAZOLO[4, 5-D]PYRIMIDINES AS CRF ANTAGONISTS

This application claims the benefit of U.S. Provisional Application No. 60/097,386, filed Aug. 21, 1998.

FIELD OF THE INVENTION

This invention relates to novel isoxazolo[4,5-d]pyrimidines, pharmaceutical compositions containing the same and methods of using same in the treatment of psychiatric disorders and neurological diseases including affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing corticotropin releasing factor (CRF), including but not limited to disorders induced or facilitated by CRF.

BACKGROUND OF THE INVENTION

Corticotropin releasing factor, a 41 amino acid peptide, is the primary physiological regulator of proopiomelanocortin (POMC)-derived peptide secretion from the anterior pituitary gland [J. Rivier et al., *Proc. Nat. Acad. Sci. (USA)* 80:4851 (1983); W. Vale et al., *Science* 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)].

There is also evidence that CRF plays a significant role in integrating the response of the immune system to physiological, psychological, and immunological stressors [J. E. Blalock, *Physiological Reviews* 69:1 (1989); J. E. Morley, Life Sci. 41:527 (1987)].

Clinical data provides evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, *Hosp. Practice* 23:59 (1988)].

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., New Eng. J. Med. 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in brain [Grigoriadis et al., *Neuropsychopharrmacology* 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn Regul. *Peptides* 16:83 (1986)]. Preliminary studies using the putative CRF receptor antagonist α-helical ovine CRF (9–41) in a variety of behavioral paradigms demonstrate that the antagonist produces "anxiolytic-like" effects that are qualitatively similar to the benzodiazepines [C. W. Berridge and A. J. Dunn, *Horm. Behav.* 21:393 (1987), *Brain Research Reviews* 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15–1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (α-helical $CRF_{9-41}$) in a variety of behavioral paradigms have demonstrated that the CRF antagonist produces "anxiolytic-like" effects qualitatively similar to the benzodiazepines [for review see G. F. Koob and K. T. Britton, In: *Corticotropin-Releasing Factor: Basic and Clinical Studies of a Neuropeptide*, E. B. De Souza and C. B. Nemeroff eds., CRC Press p221 (1990)].

EP 0,778,277 (EP '277) describes a variety of CRF antagonists including those of the formula:

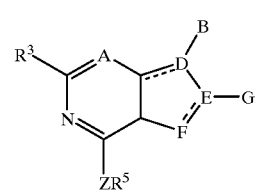

wherein A can be N or C, D can be N or C, E can be N or C, F can be N, C, S, or O, and C can be absent or a variety of groups. EP '277 does not discloses any isoxazolo[4,5-d]pyrimidines like those of the present invention.

WO 98/08847 (WO '847) describes a variety of CRF antagonists including those of the formula:

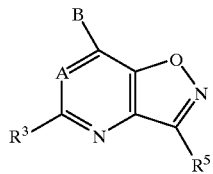

wherein A can be N or C, $R^5$ is an aromatic or heteroaromatic group, and R and $R^3$ can be a variety of groups. WO '847 does not disclose any isoxazolo[4,5-d]pyrimidines like those of the present invention.

WO 95/19774 (WO '774) describes a variety of CRF antagonists including those of the formula:

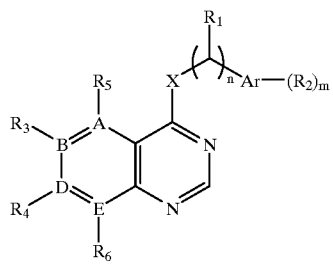

wherein A–B can be O, D can be N, and E can be C. However, WO '774 does not disclose any isoxazolo[4,5-d]pyrimidines like those of the present invention.

In view of the above, efficacious and specific antagonists of CRF are desired as potentially valuable therapeutic agents for the treatment of psychiatric disorders and neurological diseases. It is thus desirable to discover new CRF antagonists.

SUMMARY OF THE INVENTION

Accordingly, one object of the present invention is to provide novel isoxazolo[4,5-d]pyrimidines which are useful as CRF antagonists or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt form thereof.

It is another object of the present invention to provide a method for treating psychiatric disorders and neurological diseases comprising administering to a host in need of such treatment a therapeutically effective amount of at least one of the compounds of the present invention or a pharmaceutically acceptable salt form thereof.

These and other objects, which will become apparent uring the following detailed description, have been achieved by the inventors' discovery that compounds of formula I:

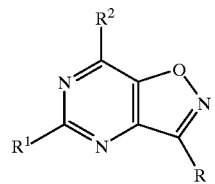

or pharmaceutically acceptable salt forms thereof, wherein R, $R^1$, and $R^2$ are defined below, are CRF antagonists.

DETAILED DESCRIPTION OF THE INVENTION

[1] A compound of formula I:

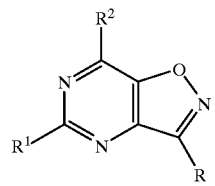

or a stereoisomer or pharmaceutically acceptable salt form thereof, wherein:

R is selected from phenyl, naphthyl, pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl and pyrazolyl, and is substituted with 0–5 $R^3$ groups;

$R^1$ is selected from H, $C_{1-4}$ alkyl, $C_{2-4}$ alkenyl, $C_{2-4}$ alkynyl, halo, —CN, $C_{1-4}$ haloalkyl, $NR^6R^7$, $NR^8COR^9$, —$OR^{10}$, SH and —$S(O)_nR^{11}$;

$R^2$ is selected from $NR^{6a}R^{7a}$ and $OR^{10a}$;

$R^3$ is independently selected at each occurrence from $C_{1-10}$ alkyl substituted with 0–2 $R^a$, $C_{2-10}$ alkenyl substituted with 0–2 $R^a$, $C_{2-10}$ alkynyl substituted with 0–2 $R^a$, $C_{3-6}$ cycloalkyl substituted with 0–2 $R^a$, ($C_{3-6}$ cycloalkyl)$C_{1-4}$ alkyl substituted with 0–2 $R^a$, —$NO_2$, halo, —CN, $C_{1-4}$ haloalkyl, —$NR^6R^7$, —$NR^8COR^{13a}$, —$NR^8C(O)OR^{13a}$, —$COR^{13}$, —$OR^{10a}$, —$CONR^6R^7$, —$NR^8CONR^6R^7$, $C(O)OR^{10a}$, SH, and —$S(O)_nR^{12}$;

$R^a$ is independently selected at each occurrence from $C_{1-4}$ alkyl, —$NO_2$, halo, —CN, —$NR^6R^7$, —$NR^8COR^{13a}$, —$NR^8C(O)OR^{13a}$, —$COR^{13}$, —$OR^{10a}$, —$CONR^6R^7$, —$NR^8CONR^6R^7$, —$C(O)OR^{10a}$, SH, and —$S(O)_nR^{12}$;

$R^6$ is independently at each occurrence selected from H, $C_{1-4}$ alkyl, $C_{3-6}$ cycloalkyl and ($C_{3-6}$ cycloalkyl)methyl;

$R^{6a}$ is independently selected at each occurrence from H, $C_{1-6}$ alkyl substituted with 0–2 $R^b$, $C_{2-6}$ alkenyl substituted with 0–2 $R^b$, $C_{2-6}$ alkynyl substituted with 0–2 $R^b$, $C_{1-4}$ haloalkyl, $C_{3-6}$ cycloalkyl substituted with 0–2 $R^b$, ($C_{3-6}$ cycloalkyl)$C_{1-4}$ alkyl substituted with 0–2 $R^b$, aryl substituted with 0–2 $R^b$, (aryl)$C_{1-4}$ alkyl substituted with 0–2 $R^b$, heteroaryl substituted with 0–2 $R^b$, (heteroaryl)$C_{1-4}$ alkyl substituted with 0–2 $R^b$, heterocyclyl substituted with 0–2 $R^b$, and (heterocyclyl)$C_{1-4}$ alkyl substituted with 0–2 $R^b$;

$R^b$ is independently selected at each occurrence from $C_{1-4}$ alkyl, —$NO_2$, halo, —CN, —$NR^{6b}R^{7a}$, —$NR^8COR^{13a}$, —$NR^8C(O)OR^{13a}$, —$COR^{13}$, —$OR^{10a}$, —$CONR^{6b}R^{7a}$, —$NR^8CONR^{6b}R^{7a}$, —$C(O)OR^{10a}$, SH, and —$S(O)_nR^{12}$;

$R^{6b}$ is independently at each occurrence selected from H, $C_{1-4}$ alkyl, $C_{3-6}$ cycloalkyl and ($C_{3-6}$ cycloalkyl)methyl;

$R^7$ is independently at each occurrence selected from H, $C_{1-4}$ alkyl, $C_{3-6}$ cycloalkyl and ($C_{3-6}$ cycloalkyl)methyl;

$R^{7a}$ is independently selected at each occurrence from H, $C_{1-6}$ alkyl, phenyl, benzyl, $C_{3-6}$ cycloalkyl, ($C_{3-6}$ cycloalkyl)methyl, and $C_{1-4}$ haloalkyl;

alternatively, $NR^{6a}R^{7a}$ is selected from piperidine, pyrrolidine, morpholine, thiomorpholine, thiomorpholine-oxide, and thiomorpholine-dioxide, and is substituted with 0–1 $R^e$;

$R^e$ is $C_{1-4}$ alkyl;

alternatively, $NR^{6a}R^{7a}$ is piperazine or N-methylpiperazine, and is substituted with 0–1 $R^f$;

$R^f$ is selected from $C_{1-4}$ alkyl, $C(O)C_{1-4}$ alkyl, $C(O)$ benzyl, $C(O)OC_{1-4}$ alkyl, $C(O)O$-benzyl, $SO_2$—$C_{1-4}$ alkyl, $SO_2$-benzyl, and $SO_2$-phenyl;

$R^8$ is independently at each occurrence selected from H, $C_{1-4}$ alkyl, $C_{3-6}$ cycloalkyl and ($C_{3-6}$ cycloalkyl)$C_{1-4}$ alkyl;

$R^9$ is independently at each occurrence selected from H, $C_{1-4}$ alkyl, $C_{3-6}$ cycloalkyl and ($C_{3-6}$ cycloalkyl)$C_{1-4}$ alkyl;

$R^{10}$ is independently at each occurrence selected from H, $C_{1-4}$ alkyl, $C_{1-4}$ haloalkyl, $C_{3-6}$ cycloalkyl, and ($C_{3-6}$ cycloalkyl)$C_{1-4}$ alkyl;

$R^{10a}$ is independently selected at each occurrence from H, $C_{1-6}$ alkyl, phenyl, benzyl, $C_{3-6}$ cycloalkyl, ($C_{3-6}$ cycloalkyl)$C_{1-4}$ alkyl, ($C_{1-4}$ alkoxy)$C_{1-4}$ alkyl, and $C_{1-4}$ haloalkyl;

$R^{10b}$ is independently selected at each occurrence from H, $C_{1-6}$ alkyl, $C_{2-4}$ alkenyl, phenyl, benzyl, $C_{3-6}$ cycloalkyl, ($C_{3-6}$ cycloalkyl)$C_{1-4}$ alkyl, ($C_{1-4}$ alkoxy)$C_{1-4}$ alkyl, and $C_{1-4}$ haloalkyl;

$R^{11}$ is independently at each occurrence selected from $C_{1-4}$ alkyl, $C_{1-4}$ haloalkyl, and $C_{3-6}$ cycloalkyl;

$R^{12}$ is independently at each occurrence selected from $C_{1-4}$ alkyl, $C_{1-4}$ haloalkyl, ($C_{1-4}$ alkoxy)$C_{1-4}$ alkyl, $C_{3-6}$ cycloalkyl, ($C_{3-6}$ cycloalkyl)$C_{1-4}$ alkyl, aryl, and (aryl)$C_{1-4}$ alkyl;

$R^{13}$ is independently at each occurrence selected from H, $C_{1-6}$ alkyl, phenyl, benzyl, $C_{3-6}$ cycloalkyl, and ($C_{3-6}$ cycloalkyl)$C_{1-4}$ alkyl;

$R^{13a}$ is independently selected at each occurrence from $C_{1-6}$ alkyl, phenyl, benzyl, $C_{3-6}$ cycloalkyl, and ($C_{3-6}$ cycloalkyl)$C_{1-4}$ alkyl;

aryl is independently at each occurrence selected from phenyl and naphthyl, and is substituted with 0–3 $R^g$;

$R^g$ is independently at each occurrence selected from $C_{1-6}$ alkyl, $C_{3-6}$ cycloalkyl, halo, $C_{1-4}$ haloalkyl, cyano, nitro, —$OR^{10a}$, SH, —$S(O)_nR^{15}$, —$COR^{16}$, —$C(O)OR^{16}$, —$OC(O))R^{17}$, $NR^8COR^{16a}$, —$NR^8CONR^{6a}R^{7a}$, —$NR^8C(O)OR^{16a}$, —$NR^{6a}R^{7a}$, and —$CONR^{6a}R^{7a}$;

$R^{15}$ is independently at each occurrence selected from $C_{1-4}$ alkyl, $C_{1-4}$ haloalkyl, ($C_{1-4}$ alkoxy)$C_{1-4}$ alkyl, $C_{3-6}$ cycloalkyl, ($C_{3-6}$ cycloalkyl)$C_{1-4}$ alkyl, phenyl, benzyl, (phenyl)$C_{1-4}$ alkyl and (naphthyl)$C_{1-4}$ alkyl;

$R^{16}$ is independently at each occurrence selected from H, $C_{1-6}$ alkyl, phenyl, benzyl, $C_{3-6}$ cycloalkyl, and ($C_{3-6}$ cycloalkyl)$C_{1-4}$ alkyl;

$R^{16a}$ is independently at each occurrence selected from $C_{1-6}$ alkyl, phenyl, benzyl, $C_{3-6}$ cycloalkyl, and ($C_{3-6}$ cycloalkyl)$C_{1-4}$ alkyl;

$R^{17}$ is independently at each occurrence selected from $C_{1-4}$ alkyl, $C_{1-4}$ haloalkyl, ($C_{1-4}$ alkoxy)$C_{1-4}$ alkyl, $C_{3-6}$ cycloalkyl, ($C_{3-6}$ cycloalkyl)$C_{1-4}$ alkyl, phenyl, benzyl, (phenyl)$C_{1-4}$ alkyl, (naphthyl)$C_{1-4}$ alkyl, heteroaryl and (heteroaryl)$C_{1-4}$ alkyl;

heteroaryl is independently at each occurrence selected from pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, and indazolyl, and is substituted with 0–3 $R^h$;

heterocyclyl is saturated or partially saturated heteroaryl, substituted with 0–3 $R^h$; and $R^h$ is independently at each occurrence selected from $C_{1-6}$ alkyl, $C_{3-6}$ cycloalkyl, halo, $C_{1-4}$ haloalkyl, cyano, nitro, —$OR^{10a}$, SH, —$S(O)_nR^{15}$, —$COR^{16}$, —$C(O)OR^{16}$, —$OC(O)R^{18}$, $NR^8COR^{16a}$, —$NR^8CONR^{6a}R^{7a}$, —$NR^8CO_2R^{16a}$, —$NR^{6a}R^{7a}$, and —$CONR^{6a}R^{7a}$;

$R^{18}$ is independently selected at each occurrence from $C_{1-6}$ alkyl, $C_{3-6}$ cycloalkyl, phenyl and benzyl; and n is independently at each occurrence selected from 0, 1 and 2.

[2] In a preferred embodiment, the present invention provides novel compounds, wherein:

R is selected from phenyl and pyridyl, and is substituted with 0–5 $R^3$ groups;

$R^1$ is selected from H, $CH_3$, $CH_2CH_3$, Cl, F, Br, —CN, $CF_3$, NH2, NH(CH3), N($CH_3$)$_2$, OH, $OCH_3$, SH, $SCH_3$, and $S(O)_2CH_3$;

$R^2$ is $NR^{6a}R^{7a}$; and, $R^3$ is independently selected at each occurrence from $C_{1-6}$ alkyl substituted with 0–2 $R^a$, $C_{2-6}$ alkenyl substituted with 0–2 $R^a$, $C_{2-6}$ alkynyl substituted with 0–2 $R^a$, $C_{3-6}$ cycloalkyl substituted with 0–2 $R^a$, ($C_{3-6}$ cycloalkyl)$C_{1-2}$ alkyl substituted with 0–2 $R^a$, —$NO_2$, halo, —CN, $C_{1-4}$ haloalkyl, —$NR^6R^7$, —$NR^8COR^{13a}$, —$COR^{13}$, —$OR^{10a}$, —$CONR^6R^7$, —$C(O)OR^{10a}$, and —$S(O)_nR^{12}$.

[3] In a more preferred embodiment, the present invention provides novel compounds, wherein:

R is selected from phenyl and pyridyl, and is substituted with 1–3 $R^3$ groups;

$R^1$ is selected from H, $CH_3$, $CH_2CH_3$, Cl, and F;

$R^3$ is independently selected at each occurrence from $C_{1-6}$ alkyl substituted with 0–2 $R^a$, $C_{2-6}$ alkenyl substituted with 0–2 $R^a$, $C_{2-6}$ alkynyl substituted with 0–2 $R^a$, $C_{3-6}$ cycloalkyl substituted with 0–2 $R^a$, ($C_{3-6}$ cycloalkyl)$C_{1-2}$ alkyl substituted with 0–2 $R^a$, F, Cl, $C_{1-4}$ haloalkyl, —$NR^6R^7$, —$NR^8COR^{13a}$, —$COR^{13}$, —$OR^{10a}$, —$CONR^6R^7$, —$C(O)OR^{10}$, and —$S(O)_nR^{12}$.

$R^a$ is independently selected at each occurrence from $C_{1-4}$ alkyl, —$NO_2$, F, Cl, —CN, —$NR^6R^7$, —$NR^8COR^{13a}$, —$COR^{13}$, —$OR^{10a}$, —$CONR^{6a}R^{7a}$, —$C(O)OR^{10a}$, and —$S(O)_nR^{12}$;

$R^{6a}$ is independently selected at each occurrence from $C_{1-6}$ alkyl substituted with 0–2 $R^b$, $C_{2-6}$ alkenyl substituted with 0–2 $R^b$, $C_{2-6}$ alkynyl substituted with 0–2 $R^b$, $C_{3-6}$ cycloalkyl substituted with 0–2 $R^b$, ($C_{3-6}$ cycloalkyl)$C_{1-4}$ alkyl substituted with 0–2 $R^b$, (aryl)

$C_{1-4}$ alkyl substituted with 0–2 $R^b$, (heteroaryl)$C_{1-4}$ alkyl substituted with 0-2 Rb, and (heterocyclyl)$C_{1-4}$ alkyl substituted with 0–2 $R^b$;

$R^b$ is independently selected at each occurrence from $C_{1-4}$ alkyl, —NO$_2$, F, Cl, —CN, —NR$^{6b}$R$^{7a}$, —NR$^8$COR$^{13a}$, —COR$^{13}$, —OR$^{10a}$, —CONR$^{6b}$R$^{7a}$, —C(O)OR$^{10a}$, and —S(O)$_n$R$^{12}$; and, $R^{7a}$ is independently selected at each occurrence from H, $C_{1-6}$ alkyl, benzyl, and ($C_{3-6}$ cycloalkyl)methyl.

[4] In an even more preferred embodiment, the present invention provides novel compounds, wherein:

$R^1$ is CH$_3$;

$R^3$ is independently selected at each occurrence from $C_{1-6}$ alkyl substituted with 0–2 $R^a$, $C_{2-6}$ alkenyl substituted with 0–2 $R^a$, $C_{2-6}$ alkynyl substituted with 0–2 $R^a$, $C_{3-6}$ cycloalkyl substituted with 0–2 $R^a$, ($C_{3-6}$ cycloalkyl)$C_{1-2}$ alkyl substituted with 0–2 $R^a$, —NO$_2$, halo, —CN, $C_{1-4}$ haloalkyl, —NR$^6$R$^7$, —NR$^8$COR$^{13a}$, —COR$^{13}$, —OR$^{10a}$, —CONR$^6$R$^7$, —C(O)OR$^{10a}$, and —S(O)$_n$R$^{12}$, $R^a$ is independently selected at each occurrence from $C_{1-4}$ alkyl, —NO$_2$, F, Cl, —CN, —NR$^6$R$^7$, —NR$^8$COR$^{13a}$, —COR$^{13}$, —OR$^{10a}$, —CONR$^6$R$^7$, —C(O)OR$^{10a}$, and —S(O)$_n$R$^{12}$;

$R^{6a}$ is independently selected at each occurrence from $C_{2-4}$ alkyl substituted with 0–2 $R^b$, ($C_{3-5}$ cycloalkyl)$C_{1-2}$ alkyl substituted with 0–2 groups selected from CH$_3$O and CH$_3$CH$_2$O, (aryl)$C_{1-2}$ alkyl substituted with 0–2 $R^b$, (heteroaryl)$C_{1-2}$ alkyl substituted with 0–2 $R^b$, and (heterocyclyl)$C_{1-2}$ alkyl substituted with 0–2 $R^b$;

$R^b$ is independently selected at each occurrence from $C_{1-4}$ alkyl, —NO$_2$, F, Cl, —CN, —NR$^{6b}$R$^{7a}$, —NR$^8$COR$^{13a}$, —COR$^{13}$, —OR$^{10a}$, —CONR$^{6b}$R$^{7a}$, —C(O)OR$^{10a}$, and —S(O)$_n$R$^{12}$;

$R^8$ is independently at each occurrence selected from H, $C_{1-4}$ alkyl, $C_{3-6}$ cycloalkyl and ($C_{3-6}$ cycloalkyl)$C_{1-2}$ alkyl;

$R^9$ is independently at each occurrence selected from H, $C_{1-4}$ alkyl, $C_{3-6}$ cycloalkyl and ($C_{3-6}$ cycloalkyl)$C_{1-2}$ alkyl;

$R^{10}$ is independently at each occurrence selected from H, $C_{1-4}$ alkyl, $C_{1-4}$ haloalkyl, $C_{3-6}$ cycloalkyl, and ($C_{3-6}$ cycloalkyl)$C_{1-2}$ alkyl;

$R^{10a}$ is independently at each occurrence selected from H, $C_{1-6}$ alkyl, phenyl, benzyl, $C_{3-6}$ cycloalkyl, ($C_{3-6}$ cycloalkyl)$C_{1-2}$ alkyl, ($C_{1-4}$ alkoxy)$C_{1-2}$ alkyl, and $C^{1-4}$ haloalkyl;

$R^{10b}$ is independently selected at each occurrence from H, $C_{1-6}$ alkyl, $C_{2-4}$ alkenyl, phenyl, benzyl, $C_{3-6}$ cycloalkyl, ($C_{3-6}$ cycloalkyl)$C_{1-2}$ alkyl, ($C_{1-4}$ alkoxy)$C_{1-2}$ alkyl, and $C_{1-4}$ haloalkyl;

$R^{11}$ is independently at each occurrence selected from $C_{1-4}$ alkyl, $C_{1-4}$ haloalkyl, and $C_{3-6}$ cycloalkyl;

$R^{12}$ is independently at each occurrence selected from $C_{1-4}$ alkyl, $C_{1-4}$ haloalkyl, ($C_{1-4}$ alkoxy)$C_{1-2}$ alkyl, $C_{3-6}$ cycloalkyl, ($C_{3-6}$ cycloalkyl)$C_{1-2}$ alkyl, aryl, and (aryl)$C_{1-2}$ alkyl;

$R^{13a}$ is independently at each occurrence selected from $C_{1-6}$ alkyl, phenyl, benzyl, $C_{3-6}$ cycloalkyl, and ($C_{3-6}$ cycloalkyl)$C_{1-2}$ alkyl;

aryl is independently at each occurrence phenyl substituted with 0–3 $R^g$;

$R^g$ is independently at each occurrence selected from $C_{1-4}$ alkyl, $C_{3-6}$ cycloalkyl, F, Cl, $C_{1-4}$ haloalkyl, cyano, nitro, —OR$^{10a}$, —S(O)$_n$R$^{15}$, —COR$^{16}$, —C(O)OR$^{16}$, —NR$^8$COR$^{16a}$, —NR$^{6a}$R$^{7a}$, and —CONR$^{6a}$R$^{7a}$;

$R^{15}$ is independently at each occurrence selected from $C_{1-4}$ alkyl, $C_{1-4}$ haloalkyl, ($C_{1-4}$ alkoxy)$C_{1-4}$ alkyl, $C_{3-6}$ cycloalkyl, ($C_{3-6}$ cycloalkyl)$C_{1-4}$ alkyl, phenyl, benzyl, and (phenyl)$C_{1-2}$ alkyl;

$R^{16}$ is independently at each occurrence selected from H, $C_{1-4}$ alkyl, phenyl, benzyl, $C_{3-6}$ cycloalkyl, and ($C_{3-6}$ cycloalkyl)$C_{1-2}$ alkyl;

$R^{16a}$ is independently at each occurrence selected from $C_{1-4}$ alkyl, phenyl, benzyl, $C_{3-6}$ cycloalkyl, and ($C_{3-6}$ cycloalkyl)$C_{1-2}$ alkyl;

heteroaryl is independently at each occurrence selected from pyridyl, pyrimidinyl, furanyl, imidazolyl, thiazolyl, pyrrolyl, oxazolyl, isoxazolyl, pyrazolyl, triazolyl, and tetrazolyl, and is substituted with 0–3 $R^h$;

heterocyclyl is saturated or partially saturated heteroaryl, substituted with 0–3 $R^h$; and, $R^h$ is independently at each occurrence selected from $C_{1-6}$ alkyl, $C_{3-6}$ cycloalkyl, F, Cl, $C_{1-4}$ haloalkyl, cyano, nitro, —OR$^{10a}$, —S(O)$_n$R$^{15}$, —COR$^{16}$, —C(O)OR$^{16}$, —NR$^8$COR$^{16a}$, —NR$^{6a}$R$^{7a}$, and —CONR$^{6a}$R$^{7a}$.

[5] In a further preferred embodiment, the present invention provides a compound selected from the group:

3-(2,4-dichlorophenyl)-5-methyl-7-(3-pentyl)amino-isoxazolo[4,5-d]pyrimidine;

3-(2,4-dichlorophenyl)-5-methyl-7-(methoxybut-2-yl) amino-isoxazolo[4,5-d]pyrimidine;

3-(2,4-dichlorophenyl)-5-methyl-7-(1,3-bis(methoxy) prop-2-yl)amino-isoxazolo[4,5-d]pyrimidine;

3-(2,4-dichlorophenyl)-5-methyl-7-(di(methoxyethyl) amino)-isoxazolo[4,5-d]pyrimidine;

3-(2,4-dichlorophenyl)-5-methyl-7-(N-ethyl-N-butyl) amino-isoxazolo[4,5-d]pyrimidine;

3-(2,4-dichlorophenyl)-5-methyl-7-(N-ethyl-N-propyl) amino-isoxazolo[4,5-d]pyrimidine;

3-(2,4-dichlorophenyl)-5-methyl-7-diethylamino-isoxazolo[4,5-d]pyrimidine;

3-(2,4-dichlorophenyl)-5-methyl-7-dipropylamino-isoxazolo[4,5-d]pyrimidine;

3-(2,4-dichlorophenyl)-5-methyl-7-(N-ethyl-N-cyclopropylmethyl)amino-isoxazolo[4,5-d]pyrimidine;

3-(2,4-dichlorophenyl)-5-methyl-7-(N-propyl-N-cyclopropylmethyl)amino-isoxazolo[4,5-d]pyrimidine;

3-(2,4-dichlorophenyl)-5-methyl-7(N-butyl-N-cyclopropylmethyl)amino-isoxazolo[4,5-d]pyrimidine;

3-(2,4-dichlorophenyl)-5-methyl-7-di(cyclopropylmethyl)amino-isoxazolo[4,5-d] pyrimidine;

3-(2,4-dichlorophenyl)-5-methyl-7-(N-ethyl-N-cyclopropyl)amino-isoxazolo[4,5-d]pyrimidine;

3-(2,4-dichlorophenyl)-5-methyl-7-(N-propyl-N-cyclopropyl)amino-isoxazolo[4,5-d]pyrimidine;

3-(2,4-dichlorophenyl)-5-methyl-7-(N-butyl-N-cyclopropyl)amino-isoxazolo[4,5-d]pyrimidine;

3-(2,4-dichlorophenyl)-5-methyl-7-dicyclopropylamino-isoxazolo[4,5-d]pyrimidine;

3-(2,4-dichlorophenyl)-5-methyl-7-(N-cyclopropyl-N-cyclopropylmethyl)amino-isoxazolo[4,5-d]pyrimidine;

3-(2,4-dichlorophenyl)-5-methyl-7-(cyclopropylbut-2-yl)amino-isoxazolo[4,5-d]pyrimidine;

3-(2,4-dichlorophenyl)-5-methyl-7-(cyclopropylpent-2-yl)amino-isoxazolo[4,5-d]pyrimidine;

3-(2,4-dichlorophenyl)-5-methyl-7-((1,3-dicyclopropyl)prop-2-yl)amino-isoxazolo[4,5-d]pyrimidine;

3-(2,4-dichlorophenyl)-5-methyl-7-(cyclopropylpropyl)amino-isoxazolo[4,5-d]pyrimidine;

3-(2,4-dichlorophenyl)-5-methyl-7-(cyclopropylbutyl)amino-isoxazolo[4,5-d]pyrimidine;

3-(2,4-dichlorophenyl)-5-methyl-7-(dicyclopropylmethyl)amino-isoxazolo[4,5-d]pyrimidine;

3-(2,4-dichlorophenyl)-5-methyl-7-((1,2-dicyclopropyl)ethyl)amino-isoxazolo[4,5-d]pyrimidine;

3-(2,4-dichlorophenyl)-5-methyl-7-(1-hydroxy-but-2-yl)amino-isoxazolo[4,5-d]pyrimidine;

3-(2,4-dichlorophenyl)-5-methyl-7-(morpholino)-isoxazolo[4,5-d]pyrimidine;

3-(2,4-dichlorophenyl)-5-methyl-7-(3-pentoxy)-isoxazolo[4,5-d]pyrimidine;

3-(2,4-dichlorophenyl)-5-methyl-7-(methoxybut-2-oxy)-isoxazolo[4,5-d]pyrimidine;

3-(2,4-dichlorophenyl)-5-methyl-7-(cyclopropylbut-2-oxy)-isoxazolo[4,5-d]pyrimidine;

3-(2,4-dichlorophenyl)-5-methyl-7-(cyclopropylpropoxy)-isoxazolo[4,5-d]pyrimidine;

3-(2,4-dichlorophenyl)-5-methyl-7-(dicyclopropylmethoxy)-isoxazolo[4,5-d]pyrimidine;

3-(2,4-dichlorophenyl)-5-methyl-7-(2-methoxy-1-cyclopropylethoxy)-isoxazolo[4,5-d]pyrimidine;

3-(2,4,6-trimethylphenyl)-5-methyl-7-(3-pentyl)amino-isoxazolo[4,5-d]pyrimidine;

3-(2,4,6-trimethylphenyl)-5-methyl-7-(methoxybut-2-yl)amino-isoxazolo[4,5-d]pyrimidine;

3-(2,4,6-trimethylphenyl)-5-methyl-7-(1,3-bis(methoxy)prop-2-yl)amino-isoxazolo[4,5-d]pyrimidine;

3-(2,4,6-trimethylphenyl)-5-methyl-7-(di(methoxyethyl)amino)-isoxazolo[4,5-d]pyrimidine;

3-(2,4,6-trimethylphenyl)-5-methyl-7-(N-ethyl-N-butyl)amino-isoxazolo[4,5-d]pyrimidine;

3-(2,4,6-trimethylphenyl)-5-methyl-7-(N-ethyl-N-propyl)amino-isoxazolo[4,5-d]pyrimidine;

3-(2,4,6-trimethylphenyl)-5-methyl-7-diethylamino-isoxazolo[4,5-d]pyrimidine;

3-(2,4,6-trimethylphenyl)-5-methyl-7-dipropylamino-isoxazolo[4,5-d]pyrimidine;

3-(2,4,6-trimethylphenyl)-5-methyl-7-(N-ethyl-N-cyclopropylmethyl)amino-isoxazolo[4,5-d]pyrimidine;

3-(2,4,6-trimethylphenyl)-5-methyl-7-(N-propyl-N-cyclopropylmethyl)amino-isoxazolo[4,5-d]pyrimidine;

3-(2,4,6-trimethylphenyl)-5-methyl-7(N-butyl-N-cyclopropylmethyl)amino-isoxazolo[4,5-d]pyrimidine;

3-(2,4,6-trimethylphenyl)-5-methyl-7-di(cyclopropylmethyl)amino-isoxazolo[4,5-d]pyrimidine;

3-(2,4,6-trimethylphenyl)-5-methyl-7-(N-ethyl-N-cyclopropyl)amino-isoxazolo[4,5-d]pyrimidine;

3-(2,4,6-trimethylphenyl)-5-methyl-7-(N-propyl-N-cyclopropyl)amino-isoxazolo[4,5-d]pyrimidine;

3-(2,4,6-trimethylphenyl)-5-methyl-7-(N-butyl-N-cyclopropyl)amino-isoxazolo[4,5-d]pyrimidine;

3-(2,4,6-trimethylphenyl)-5-methyl-7-dicyclopropylamino-isoxazolo[4,5-d]pyrimidine;

3-(2,4,6-trimethylphenyl)-5-methyl-7-(N-cyclopropyl-N-cyclopropylmethyl)amino-isoxazolo[4,5-d]pyrimidine;

3-(2,4,6-trimethylphenyl)-5-methyl-7-(cyclopropylbut-2-yl)amino-isoxazolo[4,5-d]pyrimidine;

3-(2,4,6-trimethylphenyl)-5-methyl-7-(cyclopropylpent-2-yl)amino-isoxazolo[4,5-d]pyrimidine;

3-(2,4,6-trimethylphenyl)-5-methyl-7-((1,3-dicyclopropyl)prop-2-yl)amino-isoxazolo[4,5-d]pyrimidine;

3-(2,4,6-trimethylphenyl)-5-methyl-7-(cyclopropylpropyl)amino-isoxazolo[4,5-d]pyrimidine;

3-(2,4,6-trimethylphenyl)-5-methyl-7-(cyclopropylbutyl)amino-isoxazolo[4,5-d]pyrimidine;

3-(2,4,6-trimethylphenyl)-5-methyl-7-(dicyclopropylmethyl)amino-isoxazolo[4,5-d]pyrimidine;

3-(2,4,6-trimethylphenyl)-5-methyl-7-((1,2-dicyclopropyl)ethyl)amino-isoxazolo[4,5-d]pyrimidine;

3-(2,4,6-trimethylphenyl)-5-methyl-7-(1-hydroxy-but-2-yl)amino-isoxazolo[4,5-d]pyrimidine;

3-(2,4,6-trimethylphenyl)-5-methyl-7-(morpholino)-isoxazolo[4,5-d]pyrimidine;

3-(2,4,6-trimethylphenyl)-5-methyl-7-(3-pentoxy)-isoxazolo[4,5-d]pyrimidine;

3-(2,4,6-trimethylphenyl)-5-methyl-7-(methoxybut-2-oxy)-isoxazolo[4,5-d]pyrimidine;

3-(2,4,6-trimethylphenyl)-5-methyl-7-(cyclopropylbut-2-oxy)-isoxazolo[4,5-d]pyrimidine;

3-(2,4,6-trimethylphenyl)-5-methyl-7-(cyclopropylpropoxy)-isoxazolo[4,5-d]pyrimidine;

3-(2,4,6-trimethylphenyl)-5-methyl-7-(dicyclopropylmethoxy)-isoxazolo[4,5-d]pyrimidine;

3-(2,4,6-trimethylphenyl)-5-methyl-7-(2-methoxy-1-cyclopropylethoxy)-isoxazolo[4,5-d]pyrimidine;

3-(2,4-dimethylphenyl)-5-methyl-7-(3-pentyl)amino-isoxazolo[4,5-d]pyrimidine;

3-(2,4-dimethylphenyl)-5-methyl-7-(methoxybut-2-yl)amino-isoxazolo[4,5-d]pyrimidine;

3-(2,4-dimethylphenyl)-5-methyl-7-(1,3-bis(methoxy)prop-2-yl)amino-isoxazolo[4,5-d]pyrimidine;

3-(2,4-dimethylphenyl)-5-methyl-7-(di(methoxyethyl)amino)-isoxazolo[4,5-d]pyrimidine;

3-(2,4-dimethylphenyl)-5-methyl-7-(N-ethyl-N-butyl)amino-isoxazolo[4,5-d]pyrimidine;

3-(2,4-dimethylphenyl)-5-methyl-7-(N-ethyl-N-propyl)amino-isoxazolo[4,5-d]pyrimidine;

3-(2,4-dimethylphenyl)-5-methyl-7-diethylamino-isoxazolo[4,5-d]pyrimidine;

3-(2,4-dimethylphenyl)-5-methyl-7-dipropylamino-isoxazolo[4,5-d]pyrimidine;

3-(2,4-dimethylphenyl)-5-methyl-7-(N-ethyl-N-cyclopropylmethyl)amino-isoxazolo[4,5-d]pyrimidine;

3-(2,4-dimethylphenyl)-5-methyl-7-(N-propyl-N-cyclopropylmethyl)amino-isoxazolo[4,5-d]pyrimidine;

3-(2,4-dimethylphenyl)-5-methyl-7(N-butyl-N-cyclopropylmethyl)amino-isoxazolo[4,5-d]pyrimidine;

3-(2,4-dimethylphenyl)-5-methyl-7-di(cyclopropylmethyl)amino-isoxazolo[4,5-d]pyrimidine;

3-(2,4-dimethylphenyl)-5-methyl-7-(N-ethyl-N-cyclopropyl)amino-isoxazolo[4,5-d]pyrimidine;

3-(2,4-dimethylphenyl)-5-methyl-7-(N-propyl-N-cyclopropyl)amino-isoxazolo[4,5-d]pyrimidine;

3-(2,4-dimethylphenyl)-5-methyl-7-(N-butyl-N-cyclopropyl)amino-isoxazolo[4,5-d]pyrimidine;

3-(2,4-dimethylphenyl)-5-methyl-7-dicyclopropylamino-isoxazolo[4,5-d]pyrimidine;

3-(2,4-dimethylphenyl)-5-methyl-7-(N-cyclopropyl-N-cyclopropylmethyl)amino-isoxazolo[4,5-d]pyrimidine;

3-(2,4-dimethylphenyl)-5-methyl-7-(cyclopropylbut-2-yl)amino-isoxazolo[4,5-d]pyrimidine;

3-(2,4-dimethylphenyl)-5-methyl-7-(cyclopropylpent-2-yl)amino-isoxazolo[4,5-d]pyrimidine;

3-(2,4-dimethylphenyl)-5-methyl-7-((1,3-dicyclopropyl)prop-2-yl)amino-isoxazolo[4,5-d]pyrimidine;

3-(2,4-dimethylphenyl)-5-methyl-7-(cyclopropylpropyl)amino-isoxazolo[4,5-d]pyrimidine;

3-(2,4-dimethylphenyl)-5-methyl-7-(cyclopropylbutyl)amino-isoxazolo[4,5-d]pyrimidine;

3-(2,4-dimethylphenyl)-5-methyl-7-(dicyclopropylmethyl)amino-isoxazolo[4,5-d]pyrimidine;

3-(2,4-dimethylphenyl)-5-methyl-7-((1,2-dicyclopropyl)ethyl)amino-isoxazolo[4,5-d]pyrimidine;

3-(2,4-dimethylphenyl)-5-methyl-7-(1-hydroxy-but-2-yl)amino-isoxazolo[4,5-d]pyrimidine;

3-(2,4-dimethylphenyl)-5-methyl-7-(morpholino)-isoxazolo[4,5-d]pyrimidine;

3-(2,4-dimethylphenyl)-5-methyl-7-(3-pentoxy)-isoxazolo[4,5-d]pyrimidine;

3-(2,4-dimethylphenyl)-5-methyl-7-(methoxybut-2-oxy)-isoxazolo(4,5-d]pyrimidine;

3-(2,4-dimethylphenyl)-5-methyl-7-(cyclopropylbut-2-oxy)-isoxazolo[4,5-d]pyrimidine;

3-(2,4-dimethylphenyl)-5-methyl-7-(cyclopropylpropoxy)-isoxazolo[4,5-d]pyrimidine;

3-(2,4-dimethylphenyl)-5-methyl-7-(dicyclopropylmethoxy)-isoxazolo[4,5-d]pyrimidine; and, 3-(2,4-dimethylphenyl)-5-methyl-7-(2-methoxy-1-cyclopropylethoxy)isoxazolo[4,5-d]pyrimidine; or a pharmaceutically acceptable salt form thereof.

In another embodiment, the present invention provides pharmaceutical compositions comprising a pharmaceutically acceptable carrier and a therapeutically effective amount of at least one of the compounds of the present invention or a pharmaceutically acceptable salt form thereof.

In another embodiment, the present invention provides a method of treating psychiatric disorders and neurological diseases including affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in a mammal, comprising: administering to the mammal a therapeutically effective amount of a compound of formula (I) or a pharmaceutically acceptable salt form thereof.

In another embodiment, the present invention provides intermediate compounds useful in preparation of the CRF antagonist compounds and processes for making those intermediates, as described in the following description and claims.

The CRF antagonist compounds provided by this invention and labelled derivatives thereof are also useful as standards and reagents in determining the ability of a potential pharmaceutical to bind to the CRF receptor.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e.,=O), then 2 hydrogens on the atom are replaced. Keto substituents are not present on aromatic moieties.

The present invention is intended to incclude all isotopes of atoms occurring in the present compounds. Isotopes include those atoms having the same atomic number but different mass numbers. By way of aeneral example and without limitation, isotopes of hydroaen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. "Alkenyl" is intended to include hydrocarbon chains of either a straight or branched configuration and one or more unsaturated carbon-carbon bonds which may occur in any stable point along the chain, such as ethenyl and propenyl. "Alkynyl" is intended to include hydrocarbon chains of either a straight or branched configuration and one or more triple carbon-carbon bonds which may occur in any stable point along the chain, such as ethynyl and propynyl.

"Halo" or "halogen" as used herein refers to fluoro, chloro, bromo, and iodo; and "counter-ion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

Combinations of substituents and/or variables are permissible only if such combinations result in stable compounds. A stable compound or stable structure is meant to imply a compound that is sufficiently robust to survive isolation to a useful degree of purity from a reaction mixture, and formulation into an effective therapeutic agent.

The term "therapeutically effective amount" of a compound of this invention means an amount effective to antagonize abnormal level of CRF or treat the symptoms of affective disorder, anxiety or depression in a host.

Synthesis

The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The following abbreviations are used herein:

| | |
|---|---|
| AcOH | acetic acid |
| t-BuOK | potassium tert-butoxide |
| DMSO | dimethyl sulfoxide |
| EtOAc | ethyl acetate |
| EtOH | ethanol |
| THF | tetrahydrofuran |
| TLC | thin layer chromatography |

The compounds of this invention may be prepared using the methods shown in Scheme 1. The synthesis proceeds via an α-nitroacetophenone (X) which may be prepared by C-acylation of nitromethane with aroyl phenyl esters (Synthesis, 1979, p295) or with substituted phenyl carboxylic acids (Chem. Pharm. Bull., 1981, 29(1), p259). The ketone (X) is then converted to the oxime (XI) which is treated with an alkyl oxalyl chloride to give an oxime oxalic ester. The ester is subjected to base promoted cyclization to yield isoxazole (XII) (Heterocycles, 1985, 23(6), p1465). The nitro group is then reduced using an appropriate method, for example, zinc in aqueous ammonium chloride, to produce aminoisoxazole (XIII). Amidation of the ester (XIII) may be accomplished by treatment with ammonium hydroxide to yield amide (XIV), which can be cyclized using, for example, orthoesters, to yield isoxazolopyrimidones of the formula (XV). Conversion of the hydroxy group in the tautomeric form of (XV) to a suitable leaving group may be accomplished, for example, by chlorination using, phosphorous oxychloride, or by sulfonylation (e.g., Tf$_2$O/collidine or CH$_3$SO$_2$Cl/Et$_3$N) to give a sulfonate as a leaving group. Treatment of (XVI) with amines in the presence of organic or inorganic bases provides compounds of formula (I) where R$^2$=substituted amino.

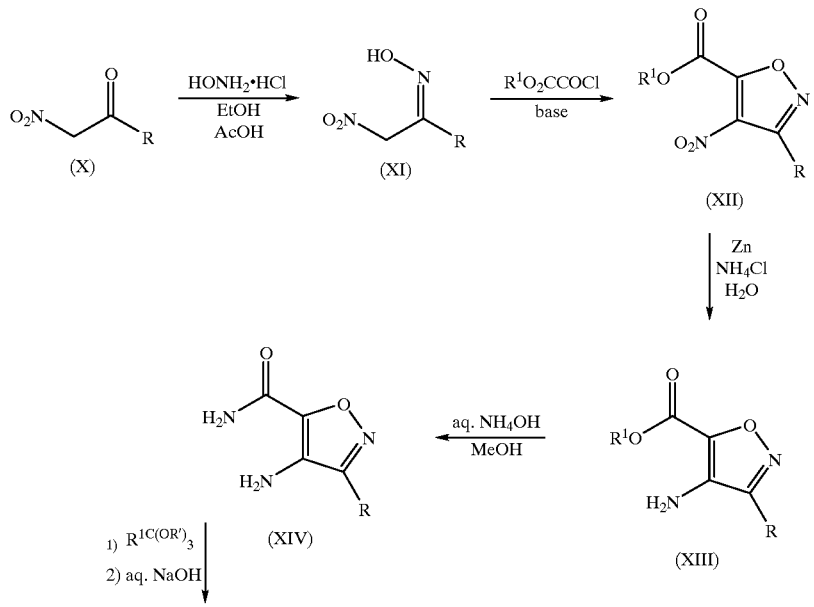

Scheme 1

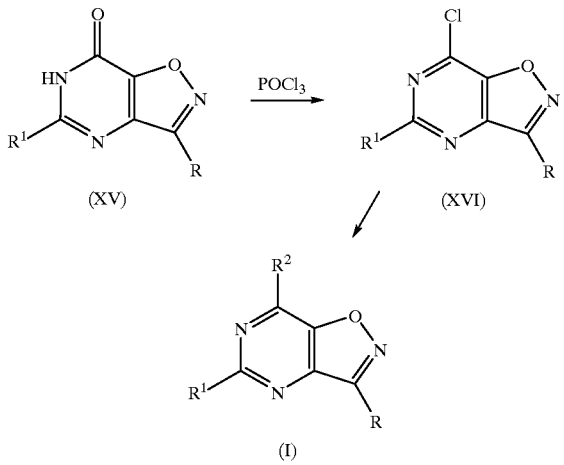

Analogous treatment of (XVI) with alcohols, optionally in the presence of bases such as NaH, provides compounds of Formula (I) where $R^2$=e.g., alkoxy.

If intermediates contain functional groups which are sensitive to reaction conditions, these groups may be protected using methods known to those skilled in the art. These methods include, but are not limited to, those described in *Protective Groups in Organic Synthesis* (Greene, Wuts; 2nd ed., 1991, John Wiley & Sons, Inc.).

The following examples are provided to describe the invention in further detail. These examples, which set forth the best mode presently contemplated for carrying out the invention, are intended to illustrate and not to limit the invention.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

3-(2,4-Dichloro-henyl)-5-methyl-7-(1-ethylpropyl) amino-isoxazolo[4, 5-d]-pyrimidine Part A: To a cooled (ice bath) solution of 2,4-dichlorobenzoyl chloride (5 mL, 35.66 mmol) in 50 mL $CH_2Cl_2$ was added phenol (3.13 mL, 35.66 mmol), followed by triethylamine (4.97 mL, 35.66 mmol). The resulting reaction mixture was stirred at room temperature for 5 h. The mixture was then partitioned between $CH_2Cl_2$ and water. The organic layer was dried ($Na_2SO_4$), filtered, and evaporated in vacuo to yield 9.5 g of phenyl 2,4-dichlorobenzoate. MS ($NH_3$-CI) 284 $(M+NH_4)^+$.

Part B: To a suspension of t-BuOK (12 g, 107 mmol) in 160 mL DMSO was cautiously added nitromethane (5.8 mL, 107 mmol) with stirring. After 1 h, phenyl 2,4-dichlorobenzoate (9.5 g, 35.6 mmol), was slowly added and the resulting reaction mixture was stirred at room temperature for 3 h. 100 mL of cold water and urea (3.3 g) were added and the mixture was cooled in and ice bath then acidified using conc. HCl (10 mL). The product was precipitated by pouring the mixture into 700 mL of water. 7.1 g of alpha-nitro-2,4-dichloroacetophenone was collected as a pale yellow solid.

$^1$H NMR (300 MHz, $CDCl_3$) δ 7.78 (d, 1H), 7.53 (m, 1H), 7.43 (m, 1H), 5.9 (s, 2H).

Part C: A mixture of alpha-nitro-2,4-dichloroacetophenone (8.3 g, 35.6 mmol)and hydroxylamine hydrochloride (2.5 g, 35.6 mmol) in ethanol (30 mL) and AcOH (10 mL) was refluxed for 7 h. The mixture was concentrated in vacuo and the residue was partitioned between EtOAc and water. The EtOAc layer was dried ($Na_2SO_4$), filtered, and evaporated in vacuo to yield 8.54 g of crude oxime. The crude product was dissolved in $Et_2O$ and ethyl oxalyl chloride (3.83 mL, 34.29 mmol) was added. The solution was stirred at room temperature for 16 h, then small amounts of triethylamine were added as product formation was monitored by TLC. When the reaction was complete, the reaction mixture was partitioned between $Et_2O$ and water. The organic layer was dried ($Na_2SO_4$), filtered, and evaporated in vacuo to yield a residue which was purified by column chromatography on silica gel (100% hexane to 50% EtOAc in hexane gradient) to yield 5.02 g of the desired nitro isoxazole.

Part D: To a cooled (ice bath) mixture of the nitroisoxazole from Example 1, Part C (4.75 g, 14.35 mmol) and $NH_4Cl$ (17.96 g, 335.69 mmol) in 75 mL of water, was added zinc dust (7.98 g, 121.98 mmol) portionwise over 15 min. The mixture was stirred for 2 h, then 20 mL of EtOAc was added and the mixture was stirred for 45 min. The mixture was filtered through celite and partitioned between EtOAc and water. The organic layer was evaporated in vacuo to afford a residue corresponding to the aminoisoxazole. MS ($NH_3$-CI) 301 $(M+H)^+$; 318 $(M+NH_3)^+$. The residue was dissolved in THF (25 mL). To this solution was added 100 mL of ammonium hydroxide and 10 mL of methanol. The mixture was stoppered and stirred at room temperature for 16 h. Volatiles were removed in vacuo and the concentrate was partitioned between EtOAc and water. The organic layer was dried ($Na_2SO_4$), filtered, and evaporated in vacuo to yield the amide. MS ($NH_3$-CI) 272 $(M+H)^+$; 289 $(M+NH_3)^+$. This crude product was refluxed in triethyl orthoacetate (50 mL) for 3 h, then concentrated in vacuo. The resulting residue was dissolved in 10 mL THF. 20 mL of 3M NaOH was added and the mixture was refluxed for 45 min, then concentrated in vacuo. The concentrate was diluted with water and AcOH was added to a pH between 5–6. This mixture was partitioned between EtOAc and water. The organic layer was evaporated in vacuo and the residue was purified by column chromatography on silica gel to give 798 mg of the desired isoxazolopyrimidone. MS (NH$_3$-CI) 296 (M+H)$^+$; 313 (M+NH$_3$)$^+$.

Part E: The isoxazolopyrimidone from Example 1, Part D (790 mg) was refluxed in 10 mL of POCl$_3$ for 3 h. The reaction mixture was concentrated in vacuo and the residue was purified by column chromatography on silica gel (100% hexane to 25% EtOAc in Hexane gradient) to give 568 mg of the chloro isoxazolopyrimidine as a pale yellow solid. MS (NH$_3$-CI) 314 (M+H)$^+$.

Part F: To a solution of 30 mg (0.095 mm ol) of the chloro isoxazolopyrimidine (Example 1, Part E) in methylene chloride (3 mL) was added a solution of 9.15 mg (0.105 mmol) of 1-ethylpropylamine in methylene chloride (0.5 mL), followed by 0.015 mL (0.105 mmol) of triethylamine. The resulting solution was stirred at room temperature for 16 h. The reaction mixture was added to a column containing silica gel and eluted (100% hexane to 25% EtOAc in Hexane gradient) to give 26 mg of the title compound as a colorless viscous oil. MS (NH$_3$-CI) 365 (M+H)$^+$. HRMS: Mass= 365.0938; Calc. Mass=365.0936 for C$_{17}$H$_{19}$N$_4$OCl$_2$ (M+H)$^+$. $^1$H NMR (300 MHz, CDCl$_3$) δ 7.82 (m, 1H), 7.6 (d, 1H, J=2.2 Hz), 7.43 (dd, 1H, J=2.2, 6.22, 1.83 Hz), 5.15 (bm, 1H), 4.32 (bm, 1H), 2.6 (s, 3H), 1.75 (m, 2H), 1.61 (m, 2H), 1.00 t, 6H, J=7.3 Hz).

Compounds in Table 1 not previously described can be made by similar procedures.

TABLE 1

| Ex. | R$^1$ | R$^2$ | R | MS$^a$ |
|---|---|---|---|---|
| 1 | CH$_3$ | NHCH(CH$_2$CH$_3$)$_2$ | 2,4-Cl$_2$Ph | 365 |
| 2 | CH$_3$ | NHCH(CH$_2$OCH$_3$)Et | 2,4-Cl$_2$Ph | 381 |
| 3 | CH$_3$ | NHCH(CH$_2$OCH$_3$)$_2$ | 2,4-Cl$_2$Ph | 397.1 |
| 4 | CH$_3$ | N(CH$_2$CH$_2$OCH$_3$)$_2$ | 2,4-Cl$_2$Ph | 411.1 |
| 5 | CH$_3$ | N(Bu)Et | 2,4-Cl$_2$Ph | 379.1 |
| 6 | CH$_3$ | N(Pr)Et | 2,4-Cl$_2$Ph | |
| 7 | CH$_3$ | N(Et)$_2$ | 2,4-Cl$_2$Ph | |
| 8 | CH$_3$ | N(Pr)$_2$ | 2,4-Cl$_2$Ph | |
| 9 | CH$_3$ | N(CH$_2$c-Pr)Et | 2,4-Cl$_2$Ph | |
| 10 | CH$_3$ | N(CH$_2$c-Pr)Pr | 2,4-Cl$_2$Ph | |
| 11 | CH$_3$ | N(CH$_2$c-Pr)Bu | 2,4-Cl$_2$Ph | |
| 12 | CH$_3$ | N(CH$_2$c-Pr)$_2$ | 2,4-Cl$_2$Ph | |
| 13 | CH$_3$ | N(c-Pr)Et | 2,4-Cl$_2$Ph | |
| 14 | CH$_3$ | N(c-Pr)Pr | 2,4-Cl$_2$Ph | |
| 15 | CH$_3$ | N(c-Pr)Bu | 2,4-Cl$_2$Ph | |
| 16 | CH$_3$ | N(c-Pr)$_2$ | 2,4-Cl$_2$Ph | |
| 17 | CH$_3$ | N(CH$_2$c-Pr)c-Pr | 2,4-Cl$_2$Ph | |
| 18 | CH$_3$ | NHCH(CH$_2$c-Pr)Et | 2,4-Cl$_2$Ph | |
| 19 | CH$_3$ | NHCH(CH$_2$c-Pr)Pr | 2,4-Cl$_2$Ph | |
| 20 | CH$_3$ | NHCH(CH$_2$c-Pr)$_2$ | 2,4-Cl$_2$Ph | |
| 21 | CH$_3$ | NHCH(c-Pr)Et | 2,4-Cl$_2$Ph | |
| 22 | CH$_3$ | NHCH(c-Pr)Pr | 2,4-Cl$_2$Ph | |
| 23 | CH$_3$ | NHCH(c-Pr)$_2$ | 2,4-Cl$_2$Ph | |
| 24 | CH$_3$ | NHCH(CH$_2$c-Pr)c-Pr | 2,4-Cl$_2$Ph | |
| 25 | CH$_3$ | NHCH(CH$_2$OH)Et | 2,4-Cl$_2$Ph | 367 |
| 26 | CH$_3$ | morpholino | 2,4-Cl$_2$Ph | 365 |
| 27 | CH$_3$ | OCH(Et)$_2$ | 2,4-Cl$_2$Ph | |
| 28 | CH$_3$ | OCH(CH$_2$OCH$_3$)Et | 2,4-Cl$_2$Ph | 382 |
| 29 | CH$_3$ | OCH(CH$_2$c-Pr)Et | 2,4-Cl$_2$Ph | |
| 30 | CH$_3$ | OCH(c-Pr)Et | 2,4-Cl$_2$Ph | |
| 31 | CH$_3$ | OCH(c-Pr)$_2$ | 2,4-Cl$_2$Ph | |
| 32 | CH$_3$ | OCH(CH$_2$OCH$_3$)c-Pr | 2,4-Cl$_2$Ph | |
| 33 | CH$_3$ | NHCH(CH$_2$CH$_3$)$_2$ | 2,4-(CH$_3$)$_2$Ph | 325.2 |
| 34 | CH$_3$ | NHCH(CH$_2$OCH$_3$)Et | 2,4-(CH$_3$)$_2$Ph | 341.2 |
| 35 | CH$_3$ | NHCH(CH$_2$OCH$_3$)$_2$ | 2,4-(CH$_3$)$_2$Ph | |
| 36 | CH$_3$ | N(CH$_2$CH$_2$OCH$_3$)$_2$ | 2,4-(CH$_3$)$_2$Ph | 371.2 |
| 37 | CH$_3$ | N(Bu)Et | 2,4-(CH$_3$)$_2$Ph | |
| 38 | CH$_3$ | N(Pr)Et | 2,4-(CH$_3$)$_2$Ph | |
| 39 | CH$_3$ | N(Et)$_2$ | 2,4-(CH$_3$)$_2$Ph | |
| 40 | CH$_3$ | N(Pr)$_2$ | 2,4-(CH$_3$)$_2$Ph | |
| 41 | CH$_3$ | N(CH$_2$c-Pr)Et | 2,4-(CH$_3$)$_2$Ph | |
| 42 | CH$_3$ | N(CH$_2$c-Pr)Pr | 2,4-(CH$_3$)$_2$Ph | |
| 43 | CH$_3$ | N(CH$_2$c-Pr)Bu | 2,4-(CH$_3$)$_2$Ph | |
| 44 | CH$_3$ | N(CH$_2$c-Pr)2 | 2,4-(CH$_3$)$_2$Ph | |
| 45 | CH$_3$ | N(c-Pr)Et | 2,4-(CH$_3$)$_2$Ph | |
| 46 | CH$_3$ | N(c-Pr)Pr | 2,4-(CH$_3$)$_2$Ph | |
| 47 | CH$_3$ | N(c-Pr)Bu | 2,4-(CH$_3$)$_2$Ph | |
| 48 | CH$_3$ | N(c-Pr)$_2$ | 2,4-(CH$_3$)$_2$Ph | |
| 49 | CH$_3$ | N(CH$_2$c-Pr)c-Pr | 2,4-(CH$_3$)$_2$Ph | |
| 50 | CH$_3$ | NHCH(CH$_2$c-Pr)Et | 2,4-(CH$_3$)$_2$Ph | |
| 51 | CH$_3$ | NHCH(CH$_2$c-Pr)Pr | 2,4-(CH$_3$)$_2$Ph | |
| 52 | CH$_3$ | NHCH(CH$_2$c-Pr)$_2$ | 2,4-(CH$_3$)$_2$Ph | |
| 53 | CH$_3$ | NHCH(c-Pr)Et | 2,4-(CH$_3$)$_2$Ph | |
| 54 | CH$_3$ | NHCH(c-Pr)Pr | 2,4-(CH$_3$)$_2$Ph | |
| 55 | CH$_3$ | NHCH(c-Pr)$_2$ | 2,4-(CH$_3$)$_2$Ph | |
| 56 | CH$_3$ | NHCH(CH$_2$c-Pr)c-Pr | 2,4-(CH$_3$)$_2$Ph | |
| 57 | CH$_3$ | NHCH(CH$_2$OH)Et | 2,4-(CH$_3$)$_2$Ph | |
| 58 | CH$_3$ | morpholino | 2,4-(CH$_3$)$_2$Ph | |
| 59 | CH$_3$ | OCH(Et)$_2$ | 2,4-(CH$_3$)$_2$Ph | |
| 60 | CH$_3$ | OCH(CH$_2$OCH$_3$)Et | 2,4-(CH$_3$)$_2$Ph | |
| 61 | CH$_3$ | OCH(CH$_2$c-Pr)Et | 2,4-(CH$_3$)$_2$Ph | |
| 62 | CH$_3$ | OCH(c-Pr)Et | 2,4-(CH$_3$)$_2$Ph | |
| 63 | CH$_3$ | OCH(c-Pr)$_2$ | 2,4-(CH$_3$)$_2$Ph | |
| 64 | CH$_3$ | OCH(CH$_2$OCH$_3$)c-Pr | 2,4-(CH$_3$)$_2$Ph | |
| 65 | CH$_3$ | NHCH(CH$_2$CH$_3$)$_2$ | 2,4,6-(CH$_3$)$_3$Ph | |
| 66 | CH$_3$ | NHCH(CH$_2$OCH$_3$)Et | 2,4,6-(CH$_3$)$_3$Ph | |
| 67 | CH$_3$ | NHCH(CH$_2$OCH$_3$)$_2$ | 2,4,6-(CH$_3$)$_3$Ph | |
| 68 | CH$_3$ | N(CH$_2$CH$_2$OCH$_3$)$_2$ | 2,4,6-(CH$_3$)$_3$Ph | |
| 69 | CH$_3$ | N(Bu)Et | 2,4,6-(CH$_3$)$_3$Ph | |
| 70 | CH$_3$ | N(Pr)Et | 2,4,6-(CH$_3$)$_3$Ph | |
| 71 | CH$_3$ | N(Et)$_2$ | 2,4,6-(CH$_3$)$_3$Ph | |
| 72 | CH$_3$ | N(Pr)$_2$ | 2,4,6-(CH$_3$)$_3$Ph | |
| 73 | CH$_3$ | N(CH$_2$c-Pr)Et | 2,4,6-(CH$_3$)$_3$Ph | |
| 74 | CH$_3$ | N(CH$_2$c-Pr)Pr | 2,4,6-(CH$_3$)$_3$Ph | |
| 75 | CH$_3$ | N(CH$_2$c-Pr)Bu | 2,4,6-(CH$_3$)$_3$Ph | |
| 76 | CH$_3$ | N(CH$_2$c-Pr)$_2$ | 2,4,6-(CH$_3$)$_3$Ph | |
| 77 | CH$_3$ | N(c-Pr)Et | 2,4,6-(CH$_3$)$_3$Ph | |
| 78 | CH$_3$ | N(c-Pr)Pr | 2,4,6-(CH$_3$)$_3$Ph | |
| 79 | CH$_3$ | N(c-Pr)Bu | 2,4,6-(CH$_3$)$_3$Ph | |
| 80 | CH$_3$ | N(c-Pr)$_2$ | 2,4,6-(CH$_3$)$_3$Ph | |
| 81 | CH$_3$ | N(CH$_2$c-Pr)c-Pr | 2,4,6-(CH$_3$)$_3$Ph | |
| 82 | CH$_3$ | NHCH(CH$_2$c-Pr)Et | 2,4,6-(CH$_3$)$_3$Ph | |
| 83 | CH$_3$ | NHCH(CH$_2$c-Pr)Pr | 2,4,6-(CH$_3$)$_3$Ph | |
| 84 | CH$_3$ | NHCH(CH$_2$c-Pr)$_2$ | 2,4,6-(CH$_3$)$_3$Ph | |
| 85 | CH$_3$ | NHCH(c-Pr)Et | 2,4,6-(CH$_3$)$_3$Ph | |
| 86 | CH$_3$ | NHCH(c-Pr)Pr | 2,4,6-(CH$_3$)$_3$Ph | |
| 87 | CH$_3$ | NHCH(c-Pr)$_2$ | 2,4,6-(CH$_3$)$_3$Ph | |
| 88 | CH$_3$ | NHCH(CH$_2$c-Pr)c-Pr | 2,4,6-(CH$_3$)$_3$Ph | |
| 89 | CH$_3$ | NHCH(CH$_2$OH)Et | 2,4,6-(CH$_3$)$_3$Ph | |
| 90 | CH$_3$ | morpholino | 2,4,6-(CH$_3$)$_3$Ph | |
| 91 | CH$_3$ | OCH(Et)$_2$ | 2,4,6-(CH$_3$)$_3$Ph | |
| 92 | CH$_3$ | OCH(CH$_2$OCH$_3$)Et | 2,4,6-(CH$_3$)$_3$Ph | |
| 93 | CH$_3$ | OCH(CH$_2$c-Pr)Et | 2,4,6-(CH$_3$)$_3$Ph | |
| 94 | CH$_3$ | OCH(c-Pr)Et | 2,4,6-(CH$_3$)$_3$Ph | |
| 95 | CH$_3$ | OCH(c-Pr)$_2$ | 2,4,6-(CH$_3$)$_3$Ph | |
| 96 | CH$_3$ | OCH(CH$_2$OCH$_3$)c-Pr | 2,4,6-(CH$_3$)$_3$Ph | |

$^a$Observed (M + H)$^+$ ion under (NH$_3$—CI) MS conditions.

Utility

Compounds of this invention are expected to have utility in the treatment of inbalances associated with abnormal levels of CRF in patients suffering from depression, affective disorders, and/or anxiety.

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 mM hygromycin. Cells surviving 4 weeks of selection in hygromycin were pooled, adapted to growth in suspension and used to generate membranes for the binding assay described below. Individual aliquots containing approximately $1 \times 10^8$ of the suspended cells were then centrifuged to form a pellet and frozen.

For the binding assay a frozen pellet described above containing 293 EBNA cells transfected with hCRFR1 receptors is homogenized in 10 ml of ice cold tissue buffer (50 mM HEPES buffer pH 7.0, containing 10 mM MgCl2, 2 mM EGTA, 1 mg/l aprotinin, 1 mg/ml leupeptin and 1 mg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 mg/ml to be used in the assay.

Binding assays are performed in 96 well plates; each well having a 300 ml capacity. To each well is added 50 ml of test drug dilutions (final concentration of drugs range from $10^{-10}$–$10^{-5}$ M), 100 ml of $^{125}$I-ovine-CRF ($^{125}$I-o-CRF) (final concentration 150 pM) and 150 ml of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.* 107:220 (1980)], which provides Ki values for inhibition which are then used to assess biological activity.

A compound is considered to be active if it has a $K_i$ value of less than about 10000 nM for the inhibition of CRF.

Inhibition of CRF-Stimulated Adenylate Cyclase Activity

Inhibition of CRF-stimulated adenylate cyclase activity can be performed as described by G. Battaglia et al. Synapse 1:572 (1987). Briefly, assays are carried out at 37° C. for 10 min in 200 ml of buffer containing 100 mM Tris-HCl (pH 7.4 at 37° C.), 10 mM MgCl$_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM OCRF, antagonist peptides (concentration range $10^{-9}$ to $10^{-6m}$) and 0.8 mg original wet weight tissue (approximately 40–60 mg protein). Reactions are initiated by the addition of 1 mM ATP/[$^{32}$p] ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 µl of [$^3$H]cAMP (approximately 40,000 dpm) is added to each tube prior to separation. The separation of [$^{32}$P]cAMP from [$^{32}$P]ATP is performed by sequential elution over Dowex and alumina columns.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990). Compounds may be tested in any species of rodent or small mammal.

Dosage and Formulation

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders;

or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent OF United States is:

1. A compound of formula (I):

or a stereoisomer or pharmaceutically acceptable salt form thereof, wherein:

R is phenyl, and is substituted with 2–5 $R^3$ groups;

$R^1$ is selected from H, $C_{1-4}$ alkyl, $C_{2-4}$ alkenyl, $C_{2-4}$ alkynyl, halo, —CN, $C_{1-4}$ haloalkyl, $NR^6R^7$, $NR^8COR^9$, —$OR^{10}$, SH and —$S(O)_nR^{11}$;

$R^2$ is $NR^{6a}R^{7a}$;

$R^3$ is independently selected at each occurrence from $C_{1-10}$ alkyl substituted with 0–2 $R^a$, $C_{2-10}$ alkenyl substituted with 0–2 $R^a$, $C_{2-10}$ alkynyl substituted with 0–2 $R^a$, $C_{3-6}$ cycloalkyl substituted with 0–2 $R^a$, ($C_{3-6}$ cycloalkyl)$C_{1-4}$ alkyl substituted with 0–2 $R^a$, —$NO_2$, halo, —CN, $C_{1-4}$ haloalkyl, —$NR^6R^7$, $NR^8COR^{13a}$, —$NR^8C(O)OR^{13a}$, —$COR^{13}$, —$OR^{10a}$, —$CONR^6R^7$, —$NR^8CONR^6R^7$, —$C(O)OR^{10a}$, SH, and —$S(O)_nR^{12}$;

$R^a$ is independently selected at each occurrence from $C_{1-4}$ alkyl, —$NO_2$, halo, —CN, —$NR^6R^7$, —$NR^8COR^{13a}$, —$NR^8C(O)OR^{13a}$, —$COR^{13}$, —$OR^{10a}$, —$CONR^6R^7$, —$NR^8CONR^6R^7$, —$C(O)OR^{10a}$, SH, and —$S(O)_nR^{12}$;

$R^6$ is independently at each occurrence selected from H, $C_{1-4}$ alkyl, $C_{3-6}$ cycloalkyl and ($C_{3-6}$ cycloalkyl)methyl;

$R^{6a}$ is independently selected at each occurrence from H, $C_{1-6}$ alkyl substituted with 0–2 $R^b$, $C_{2-6}$ alkenyl substituted with 0–2 $R^b$, $C_{2-6}$ alkynyl substituted with 0–2 $R^b$, $C_{1-4}$ haloalkyl, $C_{3-6}$ cycloalkyl substituted with 0–2 $R^b$, ($C_{3-6}$ cycloalkyl)$C_{1-4}$ alkyl substituted with 0–2 $R^b$, aryl substituted with 0–2 $R^b$, (aryl)$C_{1-4}$ alkyl substituted with 0–2 $R^b$, heteroaryl substituted with 0–2 $R^b$, (heteroaryl)$C_{1-4}$ alkyl substituted with 0–2 $R^b$, heterocyclyl substituted with 0–2 $R^b$, and (heterocyclyl)$C_{1-4}$ alkyl substituted with 0–2 $R^b$;

$R^b$ is independently selected at each occurrence from $C_{1-4}$ alkyl, —$NO_2$, halo, —CN, —$NR^{6b}R^{7a}$, —$NR^8COR^{13a}$, —$NR^8C(O)OR^{13a}$, —$COR^{13}$, —$OR^{10a}$, —$CONR^{6b}R^{7a}$, —$NR^8CONR^{6b}R^{7a}$, —$C(O)OR^{10a}$, SH, and —$S(O)_nR^{12}$;

$R^{6b}$ is independently at each occurrence selected from H, $C_{1-4}$ alkyl, $C_{3-6}$ cycloalkyl and ($C_{3-6}$ cycloalkyl)methyl;

$R^7$ is independently at each occurrence selected from H, $C_{1-4}$ alkyl, $C_{3-6}$ cycloalkyl and ($C_{3-6}$ cycloalkyl)methyl;

$R^{7a}$ is independently selected at each occurrence from H, $C_{1-6}$ alkyl, phenyl, benzyl, $C_{3-6}$ cycloalkyl, ($C_{3-6}$ cycloalkyl)methyl, and $C_{1-4}$ haloalkyl;

alternatively, $NR^{6a}R^{7a}$ is selected from piperidine, pyrrolidine, morpholine, thiomorpholine, thiomorpholine-oxide, and thiomorpholine-dioxide, and is substituted with 0–1 Re;

$R^e$ is $C_{1-4}$ alkyl;

alternatively, $NR^{6a}R^{7a}$ is piperazine or N-methylpiperazine, and is substituted with 0–1 $R^f$;

$R^f$ is selected from $C_{1-4}$ alkyl, $C(O)C_{1-4}$ alkyl, $C(O)$ benzyl, $C(O)OC_{1-4}$ alkyl, $C(O)O$-benzyl, $SO_2[\backslash M]C_{1-4}$ alkyl, $SO_2$-benzyl, and $SO_2$-phenyl;

$R^8$ is independently at each occurrence selected from H, $C_{1-4}$ alkyl, $C_{3-6}$ cycloalkyl and $(C_{3-6}$ cycloalkyl$)C_{1-4}$ alkyl;

$R^9$ is independently at each occurrence selected from H, $C_{1-4}$ alkyl, $C_{3-6}$ cycloalkyl and $(C_{3-6}$ cycloalkyl$)C_{1-4}$ alkyl;

$R^{10}$ is independently at each occurrence selected from H, $C_{1-4}$ alkyl, $C_{1-4}$ haloalkyl, $C_{3-6}$ cycloalkyl, and $(C_{3-6}$ cycloalkyl$)C_{1-4}$ alkyl;

$R^{10a}$ is independently selected at each occurrence from H, $C_{1-6}$ alkyl, phenyl, benzyl, $C_{3-6}$ cycloalkyl, $(C_{3-6}$ cycloalkyl$)C_{1-4}$ alkyl, $(C_{1-4}$ alkoxy$)C_{1-4}$ alkyl, and $C_{1-4}$ haloalkyl;

$R^{10b}$ is independently selected at each occurrence from H, $C_{1-6}$ alkyl, $C_{2-4}$ alkenyl, phenyl, benzyl, $C_{3-6}$ cycloalkyl, $(C_{3-6}$ cycloalkyl$)C_{1-4}$ alkyl, $(C_{1-4}$ alkoxy$)C_{1-4}$ alkyl, and $C_{1-4}$ haloalkyl;

$R^{11}$ is independently at each occurrence selected from $C_{1-4}$ alkyl, $C_{1-4}$ haloalkyl, and $C_{3-6}$ cycloalkyl;

$R^{12}$ is independently at each occurrence selected from $C_{1-4}$ alkyl, $C_{1-4}$ haloalkyl, $(C_{1-4}$ alkoxy$)C_{1-4}$ alkyl, $C_{3-6}$ cycloalkyl, $(C_{3-6}$ cycloalkyl$)C_{1-4}$ alkyl, aryl, and (aryl) $C_{1-4}$ alkyl;

$R^{13}$ is independently selected at each occurrence from H, $C_{1-6}$ alkyl, phenyl, benzyl, $C_{3-6}$ cycloalkyl, and $(C_{3-6}$ cycloalkyl$)C_{1-4}$ alkyl;

$R^{13a}$ is independently selected at each occurrence from $C_{1-6}$ alkyl, phenyl, benzyl, $C_{3-6}$ cycloalkyl, and $(C_{3-6}$ cycloalkyl$)C_{1-4}$ alkyl;

aryl is independently at each occurrence selected from phenyl and naphthyl, and is substituted with 0–3 $R^g$;

$R^g$ is independently at each occurrence selected from $C_{1-6}$ alkyl, $C_{3-6}$ cycloalkyl, halo, $C_{1-4}$ haloalkyl, cyano, nitro, $—OR^{10a}$, SH, $—S(O)_nR^{15}$, $—COR^{16}$, $—C(O)OR^{16}$, $—OC(O)R^{17}$, $—NR^8COR^{16a}$, $—NR^8CONR^{6a}R^{7a}$, $—NR^8C(O)OR^{16a}$, $—NR^{6a}R^{7a}$, and $—CONR^{6a}R^{7a}$;

$R^{15}$ is independently selected at each occurrence from $C_{1-4}$ alkyl, $C_{1-4}$ haloalkyl, $(C_{1-4}$ alkoxy$)C_{1-4}$ alkyl, $C_{3-6}$ cycloalkyl, $(C_{3-6}$ cycloalkyl$)C_{1-4}$ alkyl, phenyl, benzyl, (phenyl)$C_{1-4}$ alkyl and (naphthyl)$C_{1-4}$ alkyl;

$R^{16}$ is independently selected at each occurrence from H, $C_{1-6}$ alkyl, phenyl, benzyl, $C_{3-6}$ cycloalkyl, and $(C_{3-6}$ cycloalkyl$)C_{1-4}$ alkyl;

$R^{16a}$ is independently selected at each occurrence from $C_{1-6}$ alkyl, phenyl, benzyl, $C_{3-6}$ cycloalkyl, and $(C_{3-6}$ cycloalkyl$)C_{1-4}$ alkyl;

$R^{17}$ is independently selected at each occurrence from $C_{1-4}$ alkyl, $C_{1-4}$ haloalkyl, $(C_{1-4}$ alkoxy$)C_{1-4}$ alkyl, $C_{3-6}$ cycloalkyl, $(C_{3-6}$ cycloalkyl$)C_{1-4}$ alkyl, phenyl, benzyl, (phenyl)$C_{1-4}$ alkyl, (naphthyl)$C_{1-4}$ alkyl, heteroaryl and (heteroaryl)$C_{1-4}$ alkyl;

heteroaryl is independently at each occurrence selected from pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, and indazolyl, and is substituted with 0–3 $R^h$;

heterocyclyl is saturated or partially saturated heteroaryl, substituted with 0–3 $R^h$; and $R^h$ is independently at each occurrence selected from $C_{1-6}$ alkyl, $C_{3-6}$ cycloalkyl, halo, $C_{1-4}$ haloalkyl, cyano, nitro, $—OR^{10a}$, SH, $—S(O)_nR^{15}$, $—COR^{16}$, $—C(O)OR^{16}$, $—OC(O)R^{18}$, $—NR^8COR^{16a}$, $NR^8CONR^{6a}R^{7a}$, $—NR^8CO_2R^{16a}$, $—NR^{6a}R^{7a}$, and $—CONR^{6a}R^{7a}$;

$R^{18}$ is independently selected at each occurrence from $C_{1-6}$ alkyl, $C_{3-6}$ cycloalkyl, phenyl and benzyl; and n is independently at each occurrence selected from 0, 1 and 2.

2. A compound according to claim 1, wherein:

$R^1$ is selected from H, $CH_3$, $CH_2CH_3$, Cl, F, Br, $—CN$, $CF_3$, $NH_2$, $NH(CH_3)$, $N(CH_3)_2$, OH, $OCH_3$, SH, $SCH_3$, and $S(O)_2CH_3$;

$R^2$ is $NR^{6a}R^{7a}$; and, $R^3$ is independently selected at each occurrence from $C_{1-6}$ alkyl substituted with 0–2 $R^a$, $C_{2-6}$ alkenyl substituted with 0–2 $R^a$, $C_{2-6}$ alkynyl substituted with 0–2 $R^a$, $C_{3-6}$ cycloalkyl substituted with 0–2 $R^a$, $(C_{3-6}$ cycloalkyl$)C_{1-2}$ alkyl substituted with 0–2 $R^a$, $—NO_2$, halo, $—CN$, $C_{1-4}$ haloalkyl, $—NR^6R^7$, $—NR^8COR^{13a}$, $—COR^{13}$, $—OR^{10a}$, $—CONR^6R^7$, $—C(O)OR^{10a}$, and $—S(O)_nR^{12}$.

3. A compound according to claim 2, wherein:

R is phenyl, and is substituted with 2–3 $R^3$ groups;

$R^1$ is selected from H, $CH_3$, $CH_2CH_3$, Cl, and F;

$R^3$ is independently selected at each occurrence from $C_{1-6}$ alkyl substituted with 0–2 $R^a$, $C_{2-6}$ alkenyl substituted with 0–2 $R^a$, $C_{2-6}$ alkynyl substituted with 0–2 $R^a$, $C_{3-6}$ cycloalkyl substituted with 0–2 $R^a$, $(C_{3-6}$ cycloalkyl$)C_{1-2}$ alkyl substituted with 0–2 $R^a$, F, Cl, $C_{1-4}$ haloalkyl, $—NR^6R^7$, $—NR^8COR^{13a}$, $—COR^{13}$, $—OR^{10a}$, $—CONR^6R^7$, $—C(O)OR^{10}$, and $—S(O)_nR^{12}$, $R^a$ is independently selected at each occurrence from $C_{1-4}$ alkyl, $—NO2$, F, Cl, $—CN$, $—NR^6R^7$, $—NR^8COR^{13a}$, $—COR^{13}$, $—OR^{10a}$, $CONR^{6a}R^{7a}$, $—C(O)OR^{10a}$, and $—S(O)_nR^{12}$;

$R^{6a}$ is independently selected at each occurrence from $C_{1-6}$ alkyl substituted with 0–2 $R^b$, $C_{2-6}$ alkenyl substituted with 0–2 $R^b$, $C_{2-6}$ alkynyl substituted with 0–2 $R^b$, $C_{3-6}$ cycloalkyl substituted with 0–2 $R^b$, $(C_{3-6}$ cycloalkyl$)C_{1-4}$ alkyl substituted with 0–2 $R^b$, (aryl)$C_{1-4}$ alkyl substituted with 0–2 $R^b$, (heteroaryl)$C_{1-4}$ alkyl substituted with 0–2 $R^b$, and (heterocyclyl)$C_{1-4}$ alkyl substituted with 0–2 $R^b$;

$R^b$ is independently selected at each occurrence from $C_{1-4}$ alkyl, $—NO_2$, F, Cl, $—CN$, $—NR^{6b}R^{7a}$, $—NR^8COR^{13a}$, $—COR^{13}$, $—OR^{10a}$, $CONR^{6b}R^{7a}$, $—C(O)OR^{10a}$, and $—S(O)_nR^{12}$; and, $R^{7a}$ is independently selected at each occurrence from H, $C_{1-6}$ alkyl, benzyl, and $(C_{3-6}$ cycloalkyl$)$methyl.

4. A compound according to claim 3, wherein:

$R^1$ is $CH_3$;

$R^3$ is independently selected at each occurrence from $C_{1-6}$ alkyl substituted with 0–2 $R^a$, $C_{2-6}$ alkenyl substituted with 0–2 $R^a$, $C_{2-6}$ alkynyl substituted with 0–2 $R^a$, $C_{3-6}$ cycloalkyl substituted with 0–2 $R^a$, $(C_{3-6}$ cycloalkyl$)C_{1-2}$ alkyl substituted with 0–2 $R^a$, $—NO_2$, halo, $—CN$, $C_{1-4}$ haloalkyl, $—NR^6R^7$, $—NR^8COR^{13a}$, $—COR^{13}$, $—OR^{10a}$, $—CONR^6R^7$ $—C(O)OR^{10a}$, and $—S(O)_nR^{12}$, $R^a$ is independently selected at each occurrence from $C_{1-4}$ alkyl, $—NO_2$, F, Cl, $—CN$, $—NR^6R^7$, $—NR^8COR^{13a}$, $—COR^{13}$, $—OR^{10a}$, $—CONR^6R^7$, $—C(O)OR^{10a}$, and $—S(O)_nR^{12}$;

$R^{6a}$ is independently selected at each occurrence from $C_{2-4}$ alkyl substituted with 0–2 $R^b$, $(C_{3-5}$ cycloalkyl)$C_{1-2}$ alkyl substituted with 0–2 groups selected from $CH_3O$ and $CH_3CH_2O$, (aryl)$C_{1-2}$ alkyl substituted with 0–2 $R^b$, (heteroaryl)$C_{1-2}$ alkyl substituted with 0–2 $R^b$, and (heterocyclyl)$C_{1-2}$ alkyl substituted with 0–2 $R^b$;

$R^b$ is independently selected at each occurrence from $C_{1-4}$ alkyl, $-NO_2$, F, Cl, $-CN$, $-NR^{6b}R^{7a}$, $-NR^8COR^{13a}$, $-COR^{13}$, $-OR^{10a}$, $-CONR^{6b}R^{7a}$, $-C(O)OR^{10a}$, and $-S(O)R^{12}$;

$R^8$ is independently at each occurrence selected from H, $C_{1-4}$ alkyl, $C_{3-6}$ cycloalkyl and $(C_{3-6}$ cycloalkyl)$C_{1-2}$ alkyl;

$R^9$ is independently selected at each occurrence from H, $C_{1-4}$ alkyl, $C_{3-6}$ cycloalkyl and $(C_{3-6}$ cycloalkyl)$C_{1-2}$ alkyl;

$R^{10}$ is independently at each occurrence selected from H, $C_{1-4}$ alkyl, $C_{1-4}$ haloalkyl, $C_{3-6}$ cycloalkyl, and $(C_{3-6}$ cycloalkyl)$C_{1-2}$ alkyl;

$R^{10a}$ is independently selected at each occurrence from H, $C_{1-6}$ alkyl, phenyl, benzyl, $C_{3-6}$ cycloalkyl, $(C_{3-6}$ cycloalkyl)$C_{1-2}$ alkyl, $(C_{1-4}$ alkoxy)$C_{1-2}$ alkyl, and $C_{1-4}$ haloalkyl;

$R^{10b}$ is independently selected at each occurrence from H, $C_{1-6}$ alkyl, $C_{2-4}$ alkenyl, phenyl, benzyl, $C_{3-6}$ cycloalkyl, $(C_{3-6}$ cycloalkyl)$C_{1-2}$ alkyl, $(C_{1-4}$ alkoxy)$C_{1-2}$ alkyl, and $C_{1-4}$ haloalkyl;

$R^{11}$ is independently at each occurrence selected from $C_{1-4}$ alkyl, $C_{1-4}$ haloalkyl, and $C_{3-6}$ cycloalkyl;

$R^{12}$ is independently at each occurrence selected from $C_{1-4}$ alkyl, $C_{1-4}$ haloalkyl, $(C_{1-4}$ alkoxy)$C_{1-2}$ alkyl, $C_{3-6}$ cycloalkyl, $(C_{3-6}$ cycloalkyl)$C_{1-2}$ alkyl, aryl, and (aryl)1-2 alkyl;

$R^{13a}$ is independently at each occurrence selected from $C_{1-6}$ alkyl, phenyl, benzyl, $C_{3-6}$ cycloalkyl, and $(C_{3-6}$ cycloalkyl)$C_{1-2}$ alkyl;

aryl is independently at each occurrence phenyl substituted with 0–3 $R^g$;

$R^g$ is independently at each occurrence selected from $C_{1-4}$ alkyl, $C_{3-6}$ cycloalkyl, F, Cl, $C_{1-4}$ haloalkyl, cyano, nitro, $-OR^{10a}$, $-S(O)_nR^{15}$, $-COR^{16}$, $-C(O)OR^{16}$, $-NR^8COR^{16a}$, $-NR^{6a}R^{7a}$, and $-CONR^{6a}R^{7a}$;

$R^{15}$ is independently at each occurrence selected from $C_{1-4}$ alkyl, $C_{1-4}$ haloalkyl, $(C_{1-4}$ alkoxy)$C_{1-4}$ alkyl, $C_{3-6}$ cycloalkyl, $(C_{3-6}$ cycloalkyl)$C_{1-4}$ alkyl, phenyl, benzyl, and (phenyl)$C_{1-2}$ alkyl;

$R^{16}$ is independently at each occurrence selected from H, $C_{1-4}$ alkyl, phenyl, benzyl, $C_{3-6}$ cycloalkyl, and $(C_{3-6}$ cycloalkyl)$C_{1-2}$ alkyl;

$R^{16a}$ is independently at each occurrence selected from $C_{1-4}$ alkyl, phenyl, benzyl, $C_{3-6}$ cycloalkyl, and $(C_{3-6}$ cycloalkyl)$C_{1-2}$ alkyl;

heteroaryl is independently at each occurrence selected from pyridyl, pyrimidinyl, furanyl, imidazolyl, thiazolyl, pyrrolyl, oxazolyl, isoxazolyl, pyrazolyl, triazolyl, and tetrazolyl, and is substituted with 0–3 $R^h$;

heterocyclyl is saturated or partially saturated heteroaryl, substituted with 0–3 $R^h$; and, $R^h$ is independently at each occurrence selected from $C_{1-6}$ alkyl, $C_{3-6}$ cycloalkyl, F, Cl, $C_{1-4}$ haloalkyl, cyano, nitro, $-OR^{10a}$, $-S(O)_nR^{15}$, $-COR^{16}$, $-C(O)OR^{16}$, $-NR^8COR^{16a}$, $-NR^{6a}R^{7a}$, and $-CONR^{6a}R^{7a}$.

5. A compound according to claim 1, wherein the compound is selected from the group:

3-(2,4-dichlorophenyl)-5-methyl-7-(3-pentyl)amino-isoxazolo[4,5-d]pyrimnidine;

3-(2,4-dichlorophenyl)-5-methyl-7-(methoxybut-2-yl) amino-soxazolo[4,5-d]pyrimidine;

3-(2, 4-dichlorophenyl)-5-methyl-7-(1,3-bis(methoxy) prop-2-yl)amino-isoxazolo[4,5-d]pyrimidine;

3-(2,4-dichlorophenyl)-5-methyl-7-(di(methoxyethyl) amino)-isoxazolo[4,5-d]pyrimidine;

3-(2,4-dichlorophenyl)-5-methyl-7-(N-ethyl-N-butyl) amino-isoxazolo[4,5-d]pyrimidine;

3-(2,4-dichlorophenyl)-5-methyl-7-(N-ethyl-N-propyl) amnino-isoxazolo[4,5-d]pyrimidine;

3-(2,4-dichlorophenyl)-5-methyl-7-diethylamino-isoxazolo[4,5-d]pyrimidine;

3-(2,4-dichlorophenyl)-5-methyl-7-dipropylamino-isoxazolo[4,5-d]pyrimidine;

3-(2,4-dichlorophenyl)-5-methyl-7-(N-ethyl-N-cyclopropylmethyl)amino-isoxazolo[4,5-d]pyrimidine;

3-(2,4-dichlorophenyl)-5-methyl-7-(N-propyl-N-cyclopropylmethyl)amino-isoxazolo[4,5-d]pyrimidine;

3-(2,4-dichlorophenyl)-5-methyl-7(N-butyl-N-cyclopropylmethyl)amino-isoxazolo[4,5-d]pyrimidine;

3-(2,4-dichlorophenyl)-5-methyl-7-di(cyclopropylmethyl)amino-isoxazolo[4,5-d] pyrimidine;

3-(2,4-dichlorophenyl)-5-methyl-7-(N-ethyl-N-cyclopropyl)amino-isoxazolo[4,5-d]pyrimidine;

3-(2,4-dichlorophenyl)-5-methyl-7-(N-propyl-N-cyclopropyl)amino-isoxazolo[4,5-d]pyrimidine;

3-(2,4-dichlorophenyl)-5-methyl-7-(N-butyl-N-cyclopropyl)amino-isoxazolo[4,5-d]pyrimidine;

3-(2,4-dichlorophenyl)-5-methyl-7-dicyclopropylamino-isoxazolo[4,5-d]pyrimidine;

3-(2,4-dichlorophenyl)-5-methyl-7-(N-cyclopropyl-N-cyclopropylmethyl)amino-isoxazolo[4,5-d]pyrimidine;

3-(2,4-dichlorophenyl)-5-methyl-7-(cyclopropylbut-2-yl) amino-isoxazolo[4,5-d]pyrimidine;

3-(2,4-dichlorophenyl)-5-methyl-7-(cyclopropylpent-2-yl)amino-isoxazolo[4,5-d]pyrimidine;

3-(2,4-dichlorophenyl)-5-methyl-7-((1,3-dicyclopropyl) prop-2-yl)amino-isoxazolo[4,5-d]pyrimidine;

3-(2,4-dichlorophenyl)-5-methyl-7-(cyclopropylpropyl) amino-isoxazolo[4,5-d]pyrimidine;

3-(2,4-dichlorophenyl)-5-methyl-7-(cyclopropylbutyl) amino-isoxazolo[4,5-d]pyrimidine;

3-(2,4-dichlorophenyl)-5-methyl-7-(dicyclopropylmethyl)amino-isoxazolo[4,5-d] pyrimidine;

3-(2,4-dichlorophenyl)-5-methyl-7-((1,2-dicyclopropyl) ethyl)amino-isoxazolo[4,5-d]pyrimidine;

3-(2,4-dichlorophenyl)-5-methyl-7-(1-hydroxy-but-2-yl) amino-isoxazolo[4,5-d]pyrimidine;

3-(2,4-dichlorophenyl)-5-methyl-7-(morpholino)-isoxazolo[4,5-d]pyrimidine;

3-(2,4-dichlorophenyl)-5-methyl-7-(3-pentoxy)-isoxazolo[4,5-d]pyrimidine;

3-(2,4-dichlorophenyl)-5-methyl-7-(methoxybut-2-oxy)-isoxazolo[4,5-d]pyrimidine;

3-(2,4-dichlorophenyl)-5-methyl-7-(cyclopropylbut-2-oxy)-isoxazolo[4,5-d]pyrimidine;

3-(2,4-dichlorophenyl)-5-methyl-7-(cyclopropylpropoxy)-isoxazolo[4,5-d]pyrimidine;

3-(2,4-dichlorophenyl)-5-methyl-7-(dicyclopropylmethoxy)-isoxazolo[4,5-d]pyrimidine;
3-(2,4-dichlorophenyl)-5-methyl-7-(2-methoxy-1-cyclopropylethoxy)-isoxazolo[4,5-d]pyrimidine;
3-(2,4,6-trimethylphenyl)-5-methyl-7-(3-pentyl)amino-isoxazolo[4,5-d]pyrimidine;
3-(2,4,6-trimethylphenyl)-5-methyl-7-(methoxybut-2-yl)amino-isoxazolo[4,5-d]pyrimidine;
3-(2,4,6-trimethylphenyl)-5-methyl-7-(1,3-bis(methoxy)prop-2-yl)amino-isoxazolo[4,5-d]pyrimidine;
3-(2,4,6-trimethylphenyl)-5-methyl-7-(di(methoxyethyl)amino)-isoxazolo[4,5-d]pyrimidine;
3-(2,4,6-trimethylphenyl)-5-methyl-7-(N-ethyl-N-butyl)amino-isoxazolo[4,5-d]pyrimidine;
3-(2,4,6-trimethylphenyl)-5-methyl-7-(N-ethyl-N-propyl)amino-isoxazolo[4,5-d]pyrimidine;
3-(2,4,6-trimethylphenyl)-5-methyl-7-diethylamino-isoxazolo[4,5-d]pyrimidine;
3-(2,4,6-trimethylphenyl)-5-methyl-7-dipropylamino-isoxazolo[4,5-d]pyrimidine;
3-(2,4,6-trimethylphenyl)-5-methyl-7-(N-ethyl-N-cyclopropylmethyl)amino-isoxazolo[4,5-d]pyrimidine;
3-(2,4,6-trimethylphenyl)-5-methyl-7-(N-propyl-N-cyclopropylmethyl)amino-isoxazolo[4,5-d]pyrimidine;
3-(2,4,6-trimethylphenyl)-5-methyl-7(N-butyl-N-cyclopropylmethyl)amino-isoxazolo[4,5-d]pyrimidine;
3-(2,4,6-trimethylphenyl)-5-methyl-7-di(cyclopropylmethyl)amino-isoxazolo[4,5-d]pyrimidine;
3-(2,4,6-trimethylphenyl)-5-methyl-7-(N-ethyl-N-cyclopropyl)amino-isoxazolo[4,5-d]pyrimidine;
3-(2,4,6-trimethylphenyl)-5-methyl-7-(N-propyl-N-cyclopropyl)amino-isoxazolo[4,5-d]pyrimidine;
3-(2,4,6-trimethylphenyl)-5-methyl-7-(N-butyl-N-cyclopropyl)amino-isoxazolo[4,5-d]pyrimidine;
3-(2,4,6-trimethylphenyl)-5-methyl-7-dicyclopropylamino-isoxazolo[4,5-d]pyrimidine;
3-(2,4,6-trimethylphenyl)-5-methyl-7-(N-cyclopropyl-N-cyclopropylmethyl)amino-isoxazolo[4,5-d]pyrimidine;
3-(2,4,6-trimethylphenyl)-5-methyl-7-(cyclopropylbut-2-yl)amino-isoxazolo[4,5-d]pyrimidine;
3-(2,4,6-trimethylphenyl)-5-methyl-7-(cyclopropylpent-2-yl)amino-isoxazolo[4,5-d]pyrimidine;
3-(2,4,6-trimethylphenyl)-5-methyl-7-((1,3-dicyclopropyl)prop-2-yl)amino-isoxazolo[4,5-d]pyrimidine;
3-(2,4,6-trimethylphenyl)-5-methyl-7-(cyclopropylpropyl)amino-isoxazolo[4,5-d]pyrimidine;
3-(2,4,6-trimethylphenyl)-5-methyl-7-(cyclopropylbutyl)amino-isoxazolo[4,5-d]pyrimidine;
3-(2,4,6-trimethylphenyl)-5-methyl-7-(dicyclopropylmethyl)amino-isoxazolo[4,5-d]pyrimidine;
3-(2,4,6-trimethylphenyl)-5-methyl-7-((1,2-dicyclopropyl)ethyl)amino-isoxazolo[4,5-d]pyrimidine;
3-(2,4,6-trimethylphenyl)-5-methyl-7-(1-hydroxy-but-2-yl)amino-isoxazolo[4,5-d]pyrimidine;
3-(2,4,6-trimethylphenyl)-5-methyl-7-(morpholino)-isoxazolo[4,5-d]pyrimidine;
3-(2,4,6-trimethylphenyl)-5-methyl-7-(3-pentoxy)-isoxazolo[4,5-d]pyrimidine;
3-(2,4,6-trimethylphenyl)-5-methyl-7-(methoxybut-2-oxy)-isoxazolo[4,5-d]pyrimidine;
3-(2,4,6-trimethylphenyl)-5-methyl-7-(cyclopropylbut-2-oxy)-isoxazolo[4,5-d]pyrimidine;
3-(2,4,6-trimethylphenyl)-5-methyl-7-(cyclopropylpropoxy)-isoxazolo[4,5-d]pyrimidine;
3-(2,4,6-trimethylphenyl)-5-methyl-7-(dicyclopropylmethoxy)-isoxazolo[4,5-d]pyrimidine;
3-(2,4,6-trimethylphenyl)-5-methyl-7-(2-methoxy-1-cyclopropylethoxy)-isoxazolo[4,5-d]pyrimidine;
3-(2,4-dimethylphenyl)-5-methyl-7-(3-pentyl)amino-isoxazolo[4,5-d]pyrimidine;
3-(2,4-dimethylphenyl)-5-methyl-7-(methoxybut-2-yl)amino-isoxazolo[4,5-d]pyrimidine;
3-(2,4-dimethylphenyl)-5-methyl-7-(1,3-bis(methoxy)prop-2-yl)amino-isoxazolo[4,5-d]pyrimidine;
3-(2,4-dimethylphenyl)-5-methyl-7-(di(methoxyethyl)amino)-isoxazolo[4,5-d]pyrimidine;
3-(2,4-dimethylphenyl)-5-methyl-7-(N-ethyl-N-butyl)amino-isoxazolo[4,5-d]pyrimidine;
3-(2,4-dimethylphenyl)-5-methyl-7-(N-ethyl-N-propyl)amino-isoxazolo[4,5-d]pyrimidine;
3-(2,4-dimethylphenyl)-5-methyl-7-diethylamino-isoxazolo[4,5-d]pyrimidine;
3-(2,4-dimethylphenyl)-5-methyl-7-dipropylamino-isoxazolo[4,5-d]pyrimidine;
3-(2,4-dimethylphenyl)-5-methyl-7-(N-ethyl-N-cyclopropylmethyl)amino-isoxazolo[4,5-d]pyrimidine;
3-(2,4-dimethylphenyl)-5-methyl-7-(N-propyl-N-cyclopropylmethyl)amino-isoxazolo[4,5-d]pyrimidine;
3-(2,4-dimethylphenyl)-5-methyl-7(N-butyl-N-cyclopropylmethyl)amino-isoxazolo[4,5-d]pyrimidine;
3-(2,4-dimethylphenyl)-5-methyl-7-di(cyclopropylmethyl)amino-isoxazolo[4,5-d]pyrimidine;
3-(2,4-dimethylphenyl)-5-methyl-7-(N-ethyl-N-cyclopropyl)amino-isoxazolo[4,5-d]pyrimidine;
3-(2,4-dimethylphenyl)-5-methyl-7-(N-propyl-N-cyclopropyl)amino-isoxazolo[4,5-d]pyrimidine;
3-(2,4-dimethylphenyl)-5-methyl-7-(N-butyl-N-cyclopropyl)amino-isoxazolo[4,5-d]pyrimidine;
3-(2,4-dimethylphenyl)-5-methyl-7-dicyclopropylamino-isoxazolo[4,5-d]pyrimidine;
3-(2,4-dimethylphenyl)-5-methyl-7-(N-cyclopropyl-N-cyclopropylmethyl)amino-isoxazolo[4,5-d]pyrimidine;
3-(2,4-dimethylphenyl)-5-methyl-7-(cyclopropylbut-2-yl)amino-isoxazolo[4,5-d]pyrimidine;
3-(2,4-dimethylphenyl)-5-methyl-7-(cyclopropylpent-2-yl)amino-isoxazolo[4,5-d]pyrimidine;
3-(2,4-dimethylphenyl)-5-methyl-7-((1,3-dicyclopropyl)prop-2-yl)amino-isoxazolo[4,5-d]pyrimidine;
3-(2,4-dimethylphenyl)-5-methyl-7-(cyclopropylpropyl)amino-isoxazolo[4,5-d]pyrimidine;
3-(2,4-dimethylphenyl)-5-methyl-7-(cyclopropylbutyl)amino-soxazolo[4,5-d]pyrimidine;
3-(2,4-dimethylphenyl)-5-methyl-7-(dicyclopropylmethyl)amino-isoxazolo[4,5-d]pyrimidine;
3-(2,4-dimethylphenyl)-5-methyl-7-((1,2-dicyclopropyl)ethyl)amino-isoxazolo[4,5-d]pyrimidine;
3-(2,4-dimethylphenyl)-5-methyl-7-(1-hydroxy-but-2-yl)amino-isoxazolo[4,5-d]pyrimidine;

3-(2,4-dimethylphenyl)-5-methyl-7-(morpholino)-isoxazolo[4,5-d]pyrimidine;

3-(2,4-dimethylphenyl)-5-methyl-7-(3-pentoxy)-isoxazolo[4,5-d]pyrimidine;

3-(2,4-dimethylphenyl)-5-methyl-7-(methoxybut-2-oxy)-isoxazolo[4,5-d]pyrimidine;

3-(2,4-dimethylphenyl)-5-methyl-7-(cyclopropylbut-2-oxy)-isoxazolo[4,5-d]pyrimidine;

3-(2,4-dimethylphenyl)-5-methyl-7-(cyclopropylpropoxy)-isoxazolo[4,5-d]pyrimidine;

3-(2,4-dimethylphenyl)-5-methyl-7-(dicyclopropylmethoxy)-isoxazolo[4,5-d]pyrimidine; and, 3-(2,4-dimethylphenyl)-5-methyl-7-(2-methoxy-1-cyclopropylethoxy)isoxazolo[4,5-d]pyrimidine;

or a pharmaceutically acceptable salt form thereof.

6. A compound of formula (I):

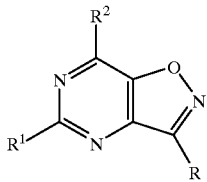

or a stereoisomer or pharmaceutically acceptable salt form thereof, wherein:

R is selected from naphthyl, pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl and pyrazolyl, and is substituted with 0–5 $R^3$ groups;

$R^1$ is selected from H, $C_{1-4}$ alkyl, $C_{2-4}$ alkenyl, $C_{2-4}$ alkynyl, halo, —CN, $C_{1-4}$ haloalkyl, $NR^6R^7$, $NR^8COR^9$, —$OR^{10}$, SH and —$S(O)_nR^{11}$;

$R^2$ is $NR^{6a}R^{7a}$;

$R^3$ is independently selected at each occurrence from $C_{1-10}$ alkyl substituted with 0–2 $R^a$, $C_{2-10}$ alkenyl substituted with 0–2 $R^a$, $C_{2-10}$ alkynyl substituted with 0–2 $R^a$, $C_{3-6}$ cycloalkyl substituted with 0–2 $R^a$, ($C_{3-6}$ cycloalkyl)$C_{1-4}$ alkyl substituted with 0–2 $R^a$, -$NO_2$, halo, —CN, $C_{1-4}$ haloalkyl, —$NR^6R^7$, —$NR^8COR^{13a}$, —$NR^8C(O)OR^{13a}$, —$COR^{13}$, —$R^{10a}$, —$CONR^6R^7$, —$NR^8CONR^6R^7$, —$C(O)OR^{10a}$, SH, and —$S(O)_nR^{12}$;

$R^a$ is independently selected at each occurrence from $C_{1-4}$ alkyl, —$NO_2$, halo, —CN, —$NR^6R^7$, —$NR^8COR^{13a}$, —$NR^8C(O)OR^{13a}$, —$COR^{13}$, —$OR^{10a}$, —$CONR^6R^7$, —$NR^8CONR^6R^7$, —$C(O)OR^{10a}$, SH, and —$S(O)_nR^{12}$;

$R^6$ is independently at each occurrence selected from H, $C_{1-4}$ alkyl, $C_{3-6}$ cycloalkyl and ($C_{3-6}$ cycloalkyl)methyl;

$R^{6a}$ is independently at each occurrence selected from H, $C_{1-6}$ alkyl substituted with 0–2 $R^b$, $C_{2-6}$ alkenyl substituted with 0–2 $R^b$, $C_{2-6}$ alkynyl substituted with 0–2 $R^b$, $C_{1-4}$ haloalkyl, $C_{3-6}$ cycloalkyl substituted with 0–2 $R^b$, ($C_{3-6}$ cycloalkyl)$C_{1-4}$ alkyl substituted with 0–2 $R^b$, aryl substituted with 0–2 $R^b$, (aryl)$C_{1-4}$ alkyl substituted with 0–2 $R^b$, heteroaryl substituted with 0–2 $R^b$, (heteroaryl)$C_{1-4}$ alkyl substituted with 0–2 $R^b$, heterocyclyl substituted with 0–2 $R^b$, and (heterocyclyl)$C_{1-4}$ alkyl substituted with 0–2 $R^b$;

$R^b$ is independently selected at each occurrence from $C_{1-4}$ alkyl, —$NO_2$, halo, —CN, —$NR^{6b}R^{7a}$, —$NR^8COR^{13a}$, $NR^8C(O)OR^{13a}$, —$COR^{13}$, —$QR^{10a}$, —$CONR^{6b}R^{7a}$, $NR^8CONR^{6b}R^{7a}$, —$C(O)OR^{10a}$, SH, and —$S(O)_nR^{12}$;

$R^{6b}$ is independently at each occurrence selected from H, $C_{1-4}$ alkyl, $C_{3-6}$ cycloalkyl and ($C_{3-6}$ cycloalkyl)methyl;

$R^7$ is independently at each occurrence selected from H, $C_{1-4}$ alkyl, $C_{3-6}$ cycloalkyl and ($C_{3-6}$ cycloalkyl)methyl;

$R^{7a}$ is independently selected at each occurrence from H, $C_{1-6}$ alkyl, phenyl, benzyl, $C_{3-6}$ cycloalkyl, ($C_{3-6}$ cycloalkyl)methyl, and $C_{1-4}$ haloalkyl;

alternatively, $NR^{6a}R^{7a}$ is selected from piperidine, pyrrolidine, morpholine, thiomorpholine, thiomorpholine-oxide, and thiomorpholine-dioxide, and is substituted with 0–1 $R^e$;

$R^e$ is $C_{1-4}$ alkyl;

alternatively, $NR^{6a}R^{7a}$ is piperazine or N-methylpiperazine, and is substituted with 0–1 $R^f$;

$R^f$ is selected from $C_{1-4}$ alkyl, $C(O)C_{1-4}$ alkyl, $C(O)$ benzyl, $C(O)OC_{1-4}$ alkyl, $C(O)O$-benzyl, $SO_2$—$C_{1-4}$ alkyl, $SO_2$-benzyl, and $SO_2$-phenyl;

$R^8$ is independently at each occurrence selected from H, $C_{1-4}$ alkyl, $C_{3-6}$ cycloalkyl and ($C_{3-6}$ cycloalkyl)$C_{1-4}$ alkyl;

$R^9$ is independently at each occurrence selected from H, $C_{1-4}$ alkyl, $C_{3-6}$ cycloalkyl and ($C_{3-6}$ cycloalkyl)$C_{1-4}$ alkyl;

$R^{10}$ is independently at each occurrence selected from H, $C_{1-4}$ alkyl, $C_{1-4}$ haloalkyl, $C_{3-6}$ cycloalkyl, and ($C_{3-6}$ cycloalkyl)$C_{1-4}$ alkyl;

$R^{10a}$ is independently selected at each occurrence from H, $C_{1-6}$ alkyl, phenyl, benzyl, $C_{3-6}$ cycloalkyl, ($C_{3-6}$ cycloalkyl)$C_{1-4}$ alkyl, ($C_{1-4}$ alkoxy)$C_{1-4}$ alkyl, and $C_{1-4}$ haloalkyl;

$R^{10b}$ is independently selected at each occurrence from H, $C_{1-6}$ alkyl, $C_{2-4}$ alkenyl, phenyl, benzyl, $C_{3-6}$ cycloalkyl, ($C_{3-6}$ cycloalkyl)$C_{1-4}$ alkyl, ($C_{1-4}$ alkoxy) $C_{1-4}$ alkyl, and $C_{1-4}$ haloalkyl;

$R^{11}$ is independently at each occurrence selected from $C_{1-4}$ alkyl, $C_{1-4}$ haloalkyl, and $C_{3-6}$ cycloalkyl;

$R^{12}$ is independently at each occurrence selected from $C_{1-4}$ alkyl, $C_{1-4}$ haloalkyl, ($C_{1-4}$ alkoxy)$C_{1-4}$ alkyl, $C_{3-6}$ cycloalkyl, ($C_{3-6}$ cycloalkyl)$C_{1-4}$ alkyl, aryl, and (aryl) $C_{1-4}$ alkyl;

$R^{13}$ is independently at each occurrence selected from H, $C_{1-6}$ alkyl, phenyl, benzyl, $C_{3-6}$ cycloalkyl, and ($C_{3-6}$ cycloalkyl)$C_{1-4}$ alkyl;

$R^{13a}$ is independently at each occurrence selected from $C_{1-6}$ alkyl, phenyl, benzyl, $C_{3-6}$ cycloalkyl, and ($C_{3-6}$ cycloalkyl)$C_{1-4}$ alkyl;

aryl is independently at each occurrence selected from phenyl and naphthyl, and is substituted with 0–3 $R^g$;

$R^g$ is independently at each occurrence selected from $C_{1-6}$ alkyl, $C_{3-6}$ cycloalkyl, halo, $C_{1-4}$ haloalkyl, cyano, nitro, —$OR^{10a}$, SH, —$S(O)_nR^{15}$, —$COR^{16}$, —$C(O)OR^{16}$, —$OC(O)R^{17}$, —$NR^8COR^{16a}$, —$NR^8CONR^{6a}R^{7a}$, —$NR^8C(O)OR^{16a}$, —$NR^{6a}R^{7a}$, and —$CONR^{6a}R^{7a}$;

$R^{15}$ is independently at each occurrence selected from $C_{1-4}$ alkyl, $C_{1-4}$ haloalkyl, ($C_{1-4}$ alkoxy)$C_{1-4}$ alkyl, $C_{3-6}$ cycloalkyl, ($C_{3-6}$ cycloalkyl)$C_{1-4}$ alkyl, phenyl, benzyl, (phenyl)$C_{1-4}$ alkyl and (naphthyl)$C_{1-4}$ alkyl;

$R^{16}$ is independently at each occurrence selected from H, $C_{1-6}$ alkyl, phenyl, benzyl, $C_{3-6}$ cycloalkyl, and ($C_{3-6}$ cycloalkyl)$C_{1-4}$ alkyl;

$R^{16a}$ is independently at each occurrence selected from $C_{1-6}$ alkyl, phenyl, benzyl, $C_{3-6}$ cycloalkyl, and $(C_{3-6}$ cycloalkyl)$C_{1-4}$ alkyl;

$R^{17}$ is independently at each occurrence selected from $C_{1-4}$ alkyl, $C_{1-4}$ haloalkyl, $(C_{1-4}$ alkoxy)$C_{1-4}$ alkyl, $C_{3-6}$ cycloalkyl, $(C_{3-6}$ cycloalkyl)$C_{1-4}$ alkyl, phenyl, benzyl, (phenyl)$C_{1-4}$ alkyl, (naphthyl)$C_{1-4}$ alkyl, heteroaryl and (heteroaryl)$C_{1-4}$ alkyl;

heteroaryl is independently at each occurrence selected from pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, and indazolyl, and is substituted with 0–3 $R^h$;

heterocyclyl is saturated or partially saturated heteroaryl, substituted with 0–3 $R^h$; and $R^h$ is independently at each occurrence selected from $C_{1-6}$ alkyl, $C_{3-6}$ cycloalkyl, halo, $C_{1-4}$ haloalkyl, cyano, nitro, —OR$^{10a}$, SH, —S(O)$_n$R$^{15}$, —COR$^{16}$, —C(O)OR$^{16}$, —OC(O)R$^{18}$, —NR$^8$COR$^{16a}$, —NR$^8$CONR$^{6a}$R$^{7a}$, —NR$^8$CO$_2$R$^{16a}$, —NR$^{6a}$R$^{7a}$, and —CONR$^{6a}$R$^{7a}$;

$R^{18}$ is independently selected at each occurrence from $C_{1-6}$ alkyl, $C_{3-6}$ cycloalkyl, phenyl and benzyl; and n is independently at each occurrence selected from 0, 1 and 2.

7. A compound according to claim 6, wherein:

R is pyridyl, and is substituted with 0–5 $R^3$ groups;

$R^1$ is selected from H, $CH_3$, $CH_2CH_3$, Cl, F, Br, —CN, $CF_3$, $NH_2$, $NH(CH_3)$, $N(CH_3)_2$, OH, $OCH_3$, SH, $SCH_3$, and $S(O)_2CH_3$;

$R^2$ is NR$^{6a}$R$^{7a}$; and, $R^3$ is independently selected at each occurrence from $C_{1-6}$ alkyl substituted with 0–2 $R^a$, $C_{2-6}$ alkenyl substituted with 0–2 $R^a$, $C_{2-6}$ alkynyl substituted with 0–2 $R^a$, $C_{3-6}$ cycloalkyl substituted with 0–2 $R^a$, $(C_{3-6}$ cycloalkyl)$C_{1-2}$ alkyl substituted with 0–2 $R^a$, —NO$_2$, halo, —CN, $C_{1-4}$ haloalkyl, —NR$^6$R$^7$, —NR$^8$COR$^{13a}$, —COR$^{13}$, —OR$^{10a}$, —CONR$^6$R$^7$, —C(O)OR$^{10a}$, and —S(O)$_n$R$^{12}$.

8. A compound according to claim 7, wherein:

R is pyridyl, and is substituted with 1–3 $R^3$ groups;

$R^1$ is selected from H, $CH_3$, $CH_2CH_3$, Cl, and F;

$R^3$ is independently selected at each occurrence from $C_{1-6}$ alkyl substituted with 0–2 $R^a$, $C_{2-6}$ alkenyl substituted with 0–2 $R^a$, $C_{2-6}$ alkynyl substituted with 0–2 $R^a$, $C_{3-6}$ cycloalkyl substituted with 0–2 $R^a$, $(C_{3-6}$ cycloalkyl)$C_{1-2}$ alkyl substituted with 0–2 $R^a$, F, Cl, $C_{1-4}$ haloalkyl, —NR$^6$R$^7$, —NR$_8$COR$^{13a}$, —COR$^{13}$, —OR$^{10a}$, —CONR$^6$R$^7$, —C(O)OR$^{10}$, and —S(O)$_n$R$^{12}$;

$R^a$ is independently selected at each occurrence from $C_{1-4}$ alkyl, —NO$_2$, F, Cl, —CN, —NR$^6$R$^7$, —NR$^8$COR$^{13a}$, —COR$^{13}$, —OR$^{10a}$, —CONR$^{6a}$R$^{7a}$, —C(O)OR$^{10a}$, and —S(O)$_n$R$^{12}$;

$R^{6a}$ is independently selected at each occurrence from $C_{1-6}$ alkyl substituted with 0–2 $R^b$, $C_{2-6}$ alkenyl substituted with 0–2 $R^b$, $C_{2-6}$ alkynyl substituted with 0–2 $R^b$, $C_{3-6}$ cycloalkyl substituted with 0–2 $R^b$, $(C_{3-6}$ cycloalkyl)$C_{1-4}$ alkyl substituted with 0–2 $R^b$, (aryl)$C_{1-4}$ alkyl substituted with 0–2 $R^b$, (heteroaryl)$C_{1-4}$ alkyl substituted with 0–2 $R^b$, and (heterocyclyl)$C_{1-4}$ alkyl substituted with 0–2 $R^b$;

$R^b$ is independently selected at each occurrence from $C_{1-4}$ alkyl, —NO$_2$, F, Cl, —CN, —NR$^{6b}$R$^{7a}$, NR$^8$COR$^{13a}$, —COR$^{13}$, —R$^{10a}$, CONR$^{6b}$R$^{7a}$, —C(O)OR$^{10a}$, and —S(O)$_n$R$^{12}$; and, $R^{7a}$ is independently selected at each occurrence from H, $C_{1-6}$ alkyl, benzyl, and $(C_{3-6}$ cycloalkyl)methyl.

9. A compound according to claim 8, wherein:

$R^1$ is $CH_3$;

$R^3$ is independently selected at each occurrence from $C_{1-6}$ alkyl substituted with 0–2 $R^a$, $C_{2-6}$ alkenyl substituted with 0–2 $R^a$, $C_{2-6}$ alkynyl substituted with 0–2 $R^a$, $C_{3-6}$ cycloalkyl substituted with 0–2 $R^a$, $(C_{3-6}$ cycloalkyl) CO12 alkyl substituted with 0–2 $R^a$, —NO$_2$, halo, —CN, $C_{1-4}$ haloalkyl, —NR$^6$R$^7$, —NR$^8$COR$^{13a}$, —COR$^{13}$, —OR$^{10a}$, —CONR$^6$R$^7$, —C(O)OR$^{10a}$, and —S(O)$_n$R$^{12}$;

$R^a$ is independently selected at each occurrence from $C_{1-4}$ alkyl, —NO$_2$, F, Cl, —CN, —NR$^6$R$^7$, —NR$^8$COR$^{13a}$, —COR$^{13}$, —OR$^{10a}$, —CONR$^6$R$^7$, —C(O)OR$^{10a}$, and —S(O)$_n$R$^{12}$;

$R^{6a}$ is independently selected at each occurrence from $C_{2-4}$ alkyl substituted with 0–2 $R^b$, $(C_{3-5}$ cycloalkyl)$C_{1-2}$ alkyl substituted with 0–2 groups selected from $CH_3O$ and $CH_3CH_2O$ (aryl)$C_{1-2}$ alkyl substituted with 0–2 $R^b$, (heteroaryl)$C_{1-2}$ alkyl substituted with 0–2 $R^b$, and (heterocyclyl)$C_{1-2}$ alkyl substituted with 0–2 $R^b$;

$R^b$ is independently selected at each occurrence from $C_{1-4}$ alkyl, —NO$_2$, F, Cl, —CN, —NR$^{6b}$R$^{7a}$, NR$^8$COR$^{13a}$, —COR$^{13}$, —OR$^{10a}$, CONR$^{6b}$R$^{7a}$, —C(O)OR$^{10a}$, and —S(O)$_n$R$^{12}$;

$R^8$ is independently at each occurrence selected from H, $C_{1-4}$ alkyl, $C_{3-6}$ cycloalkyl and $(C_{3-6}$ cycloalkyl)$C_{1-2}$ alkyl;

$R^9$ is independently at each occurrence selected from H, $C_{1-4}$ alkyl, $C_{3-6}$ cycloalkyl and $(C_{3-6}$ cycloalkyl)$C_{1-2}$ alkyl;

$R^{10}$ is independently at each occurrence selected from H, $C_{1-4}$ alkyl, $C_{1-4}$ haloalkyl, $C_{3-6}$ cycloalkyl, and $(C_{3-6}$ cycloalkyl)$C_{1-2}$ alkyl;

$R^{10a}$ is independently at each occurrence selected from H, $C_{1-6}$ alkyl, phenyl, benzyl, $C_{3-6}$ cycloalkyl, $(C_{3-6}$ cycloalkyl)$C_{1-2}$ alkyl, $(C_{1-4}$ alkoxy)$C_{1-2}$ alkyl, and $C_{1-4}$ haloalkyl;

$R^{10b}$ is independently at each occurrence selected from H, $C_{1-6}$ alkyl, $C_{2-4}$ alkenyl, phenyl, benzyl, $C_{3-6}$ cycloalkyl, $(C_{3-6}$ cycloalkyl)$C_{1-2}$ alkyl, $(C_{1-4}$ alkoxy)$C_{1-2}$ alkyl, and $C_{1-4}$ haloalkyl;

$R^{11}$ is independently at each occurrence selected from $C_{1-4}$ alkyl, $C_{1-4}$ haloalkyl, and $C_{3-6}$ cycloalkyl;

$R^{12}$ is independently at each occurrence selected from $C_{1-4}$ alkyl, $C_{1-4}$ haloalkyl, $(C_{1-4}$ alkoxy)$C_{1-2}$ alkyl, $C_{3-6}$ cycloalkyl, $(C_{3-6}$ cycloalkyl)$C_{1-2}$ alkyl, aryl, and (aryl)$C_{1-2}$ alkyl;

$R^{13a}$ is independently at each occurrence selected from $C_{1-6}$ alkyl, phenyl, benzyl, $C_{3-6}$ cycloalkyl, and $(C_{3-6}$ cycloalkyl)$C_{0-2}$ alkyl;

aryl is independently at each occurrence phenyl substituted with 0–3 $R^g$;

$R^g$ is independently at each occurrence selected from $C_{1-4}$ alkyl, $C_{3-6}$ cycloalkyl, F, Cl, $C_{1-4}$ haloalkyl, cyano, nitro, —OR$^{10a}$, —S(O)$_n$R$^{15}$, —COR$^{16}$, —C(O)OR$^{16}$, —NR$^8$COR$^{16a}$, —NR$^{6a}$R$^{7a}$, and —CONR$^{6a}$R$^{7a}$;

$R^{15}$ is independently at each occurrence selected from $C_{1-4}$ alkyl, $C_{1-4}$ haloalkyl, $(C_{1-4}$ alkoxy)$C_{1-4}$ alkyl, $C_{3-6}$ cycloalkyl, (C$_{3-6}$ cycloalkyl)C$_{1-4}$ alkyl, phenyl, benzyl, and (phenyl)C$_{1-2}$ alkyl;

R$^{16}$ is independently at each occurrence selected from H, C$_{1-4}$ alkyl, phenyl, benzyl, C$_{3-6}$ cycloalkyl, and (C$_{3-6}$ cycloalkyl)C$_{1-2}$ alkyl;

R$^{16a}$ is independently at each occurrence selected from C$_{1-4}$ alkyl, phenyl, benzyl, C$_{3-6}$ cycloalkyl, and (C$_{3-6}$ cycloalkyl)C$_{1-2}$ alkyl;

heteroaryl is independently at each occurrence selected from pyridyl, pyrimidinyl, furanyl, imidazolyl, thiazolyl, pyrrolyl, oxazolyl, isoxazolyl, pyrazolyl, triazolyl, and tetrazolyl, and is substituted with 0–3 R$^h$;

heterocyclyl is saturated or partially saturated heteroaryl, substituted with 0–3 R$^h$; and, R$^h$ is independently at each occurrence selected from C$_{1-6}$ alkyl, C$_{3-6}$ cycloalkyl, F, Cl, C$_{1-4}$ haloalkyl, cyano, nitro, —OR$^{10a}$, —S(O)$_n$R$^{15}$, —COR$^{16}$, —C(O)OR$^{16}$, —NR$^8$COR$^{16a}$, —NR$^{6a}$R$^{7a}$, and —CONR$^{6a}$R$^{7a}$.

10. A compound of formula (I):

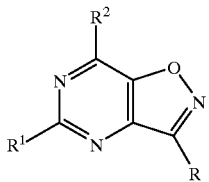

I or a stereoisomer or pharmaceutically acceptable salt form thereof, wherein:

R is phenyl, and is substituted with 1–5 R$^3$ groups;

R$^1$ is selected from H, C$_{2-4}$ alkyl, C$_{2-4}$ alkenyl, C$_{2-4}$ alkynyl, halo, —CN, C$_{1-4}$ haloalkyl, NR$^6$R$^7$, NR$^8$COR$^9$, —OR$^{10}$, SH and —S(O)$_n$R$^{11}$;

R$^2$ is NR$^{6a}$R$^{7a}$;

R$^3$ is independently selected at each occurrence from C$_{1-10}$ alkyl substituted with 0–2 R$^a$, C$_{2-10}$ alkenyl substituted with 0–2 R$^a$, C$_{2-10}$ alkynyl substituted with 0–2 R$^a$, C$_{3-6}$ cycloalkyl substituted with 0–2 R$^a$, (C$_{3-6}$ cycloalkyl)C$_{1-4}$ alkyl substituted with 0–2 R$^a$, —NO$_2$, halo, —CN, C$_{1-4}$ haloalkyl, —NR$^6$R$^7$, —NR$^8$COR$^{13a}$, —NR$^8$C(O)OR$^{13a}$, —COR$^{13}$, —OR$^{10a}$, —CONR$^6$R$^7$, —NR$^8$CONR$^6$R$^7$, C(O)OR$^{10a}$, SH, and —S(O)$_n$R$^{12}$;

R$^a$ is independently selected at each occurrence from C$_{1-4}$ alkyl, —NO$_2$, halo, —CN, —NR$^6$R$^7$, —NR$^8$COR$^{13a}$, —NR$^8$C(O)OR$^{13a}$, —COR$^{13}$, —OR$^{10a}$, —CONR$^6$R$^7$, —NR$^8$CONR$^6$R$^7$, C(O)OR$^{10a}$, SH, and —S(O)$_n$R$^{12}$;

R$^6$ is independently at each occurrence selected from H, C$_{1-4}$ alkyl, C$_{3-6}$ cycloalkyl and (C$_{3-6}$ cycloalkyl) methyl;

R$^{6a}$ is independently at each occurrence selected from H, C$_{1-6}$ alkyl substituted with 0–2 R$^b$, C$_{2-6}$ alkenyl substituted with 0–2 R$^b$, C$_{2-6}$ alkynyl substituted with 0–2 R$^b$, C$_{1-4}$ haloalkyl, C$_{3-6}$ cycloalkyl substituted with 0–2 R$^b$, (C$_{3-6}$ cycloalkyl)C$_{1-4}$ alkyl substituted with 0–2 R$^b$, aryl substituted with 0–2 R$^b$, (aryl)C$_{1-4}$ alkyl substituted with 0–2 R$^b$, heteroaryl substituted with 0–2 R$^b$, (heteroaryl)C$_{1-4}$ alkyl substituted with 0–2 R$^b$, heterocyclyl substituted with 0–2 R$^b$, and (heterocyclyl)C$_{1-4}$ alkyl substituted with 0–2 R$^b$;

R$^b$ is independently selected at each occurrence from C$_{1-4}$ alkyl, —NO$_2$, halo, —CN, —NR$^{6b}$R$^{7a}$, NR$^8$COR$^{13a}$, NR$^8$C(O)OR$^{13a}$, —COR$^{13}$, —OR$^{10a}$, —CONR$^{6b}$R$^{7a}$NR$^8$CONR$^{6b}$R$^{7a}$, —C(O)OR$^{10a}$, SH, and —S(O)$_n$R$^{12}$;

R$^{6b}$ is independently at each occurrence selected from H, C$_{1-4}$ alkyl, C$_{3-6}$ cycloalkyl and (C$_{3-6}$ cycloalkyl) methyl;

R$^7$ is independently at each occurrence selected from H, C$_{1-4}$ alkyl, C$_{3-6}$ cycloalkyl and (C$_{3-6}$ cycloalkyl) methyl;

R$^{7a}$ is independently selected at each occurrence from H, C$_{1-6}$ alkyl, phenyl, benzyl, C$_{3-6}$ cycloalkyl, (C$_{3-6}$ cycloalkyl)methyl, and C$_{1-4}$ haloalkyl;

alternatively, NR$^{6a}$R$^{7a}$ is selected from piperidine, pyrrolidine, morpholine, thiomorpholine, thiomorpholine-oxide, and thiomorpholine-dioxide, and is substituted with 0–1 R$^e$;

R$^e$ is C$_{1-4}$ alkyl;

alternatively, NR$^{6a}$R$^{7a}$ is piperazine or N-methylpiperazine, and is substituted with 0–1 R$^f$;

R$^f$ is selected from C$_{1-4}$ alkyl, C(O)C$_{1-4}$ alkyl, C(O) benzyl, C(O)OC$_{1-4}$ alkyl, C(O)O-benzyl, SO$_2$—C$_{1-4}$ alkyl, SO$_2$-benzyl, and SO$_2$-phenyl;

R$^8$ is independently at each occurrence selected from H, C$_{1-4}$ alkyl, C$_{3-6}$ cycloalkyl and (C$_{3-6}$ cycloalkyl)C$_{1-4}$ alkyl;

R$^9$ is independently at each occurrence selected from H, C$_{1-4}$ alkyl, C$_{3-6}$ cycloalkyl and (C$_{3-6}$ cycloalkyl)C$_{1-4}$ alkyl;

R$^{10}$ is independently at each occurrence selected from H, C$_{1-4}$ alkyl, C$_{1-4}$ haloalkyl, C$_{3-6}$ cycloalkyl, and (C$_{3-6}$ cycloalkyl)C$_{1-4}$ alkyl;

R$^{10a}$ is independently selected at each occurrence from H, C$_{1-6}$ alkyl, phenyl, benzyl, C$_{3-6}$ cycloalkyl, (C$_{3-6}$ cycloalkyl)C$_{1-4}$ alkyl, (C$_{1-4}$ alkoxy)C$_{1-4}$ alkyl, and C$_{1-4}$ haloalkyl;

R$^{10b}$ is independently selected at each occurrence from H, C$_{1-6}$ alkyl, C$_{2-4}$ alkenyl, phenyl, benzyl, C$_{3-6}$ cycloalkyl, (C$_{3-6}$ cycloalkyl)C$_{1-4}$ alkyl, (C$_{1-4}$ alkoxy) C$_{1-4}$ alkyl, and C$_{1-4}$ haloalkyl;

R$^{11}$ is independently at each occurrence selected from C$_{1-4}$ alkyl, C$_{1-4}$ haloalkyl, and C$_{3-6}$ cycloalkyl;

R$^{12}$ is independently at each occurrence selected from C$_{1-4}$ alkyl, C$_{1-4}$ haloalkyl, (C$_{1-4}$ alkoxy)C$_{1-4}$ alkyl, C$_{3-6}$ cycloalkyl, (C$_{3-6}$ cycloalkyl)C$_{1-4}$ alkyl, aryl, and (aryl) C$_{1-4}$ alkyl;

R$^{13}$ is independently at each occurrence selected from H, C$_{1-6}$ alkyl, phenyl, benzyl, C$_{3-6}$ cycloalkyl, and (C$_{3-6}$ cycloalkyl)C$_{1-4}$ alkyl;

R$^{13a}$ is independently at each occurrence selected from C$_{1-6}$ alkyl, phenyl, benzyl, C$_{3-6}$ cycloalkyl, and (C$_{3-6}$ cycloalkyl)C$_{1-4}$ alkyl;

aryl is independently at each occurrence selected from phenyl and naphthyl, and is substituted with 0–3 R$^g$;

R$^g$ is independently at each occurrence selected from C$_{1-6}$ alkyl, C$_{3-6}$ cycloalkyl, halo, C$_{1-4}$ haloalkyl, cyano, nitro, —OR$^{10a}$, SH, —S(O)$_n$R$^{15}$, —COR$^{16}$, —C(O) OR$^{16}$, —OC(O)R$^{17}$, NR$^8$COR$^{16a}$, NR$^8$CONR$^{6a}$R$^{7a}$, —NR$^8$C(O)OR$^{16a}$, —NR$^{6a}$R$^{7a}$, and —CONR$^{6a}$R$^{7a}$;

R$^{15}$ is independently at each occurrence selected from C$_{1-4}$ alkyl, C$_{1-4}$ haloalkyl, (C$_{1-4}$ alkoxy)C$_{1-4}$ alkyl, C$_{3-6}$ cycloalkyl, (C$_{3-6}$ cycloalkyl)C$_{1-4}$ alkyl, phenyl, benzyl, (phenyl)C$_{1-4}$ alkyl and (naphthyl)C$_{1-4}$ alkyl;

R$^{16}$ is independently at each occurrence selected from H, C$_{1-6}$ alkyl, phenyl, benzyl, C$_{3-6}$ cycloalkyl, and (C$_{3-6}$ cycloalkyl)C$_{1-4}$ alkyl;

$R^{16a}$ is independently at each occurrence selected from $C_{1-6}$ alkyl, phenyl, benzyl, $C_{3-6}$ cycloalkyl, and ($C_{3-6}$ cycloalkyl)$C_{1-4}$ alkyl;

$R^{17}$ is independently at each occurrence selected from $C_{1-4}$ alkyl, $C_{1-4}$ haloalkyl, ($C_{1-4}$ alkoxy)$C_{1-4}$ alkyl, $C_{3-6}$ cycloalkyl, ($C_{3-6}$ cycloalkyl)$C_{1-4}$ alkyl, phenyl, benzyl, (phenyl)$C_{1-4}$ alkyl, (naphthyl)$C_{1-4}$ alkyl, heteroaryl and (heteroaryl)$C_{1-4}$ alkyl;

heteroaryl is independently at each occurrence selected from pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, and indazolyl, and is substituted with 0–3 $R^h$;

heterocyclyl is saturated or partially saturated heteroaryl, substituted with 0–3 $R^h$; and $R^h$ is independently at each occurrence selected from $C_{1-6}$ alkyl, $C_{3-6}$ cycloalkyl, halo, $C_{1-4}$ haloalkyl, cyano, nitro, —$OR^{10a}$, SH, —$S(O)_nR^{15}$, —$COR^{16}$, —$C(O)OR^{16}$, —$OC(O)R^{18}$, —$NR^8COR^{16a}$, —$NR^8CONR^{6a}R^{7a}$, —$NR^8CO_2R^{16a}$, —$NR^{6a}R^{7a}$, and —$CONR^{6a}R^{7a}$;

$R^{18}$ is independently selected at each occurrence from $C_{1-6}$ alkyl, $C_{3-6}$ cycloalkyl, phenyl and benzyl; and n is independently at each occurrence selected from 0, 1 and 2.

11. A compound according to claim 10, wherein:

R is phenyl, and is substituted with 1–5 $R^3$ groups;

$R^1$ is selected from H, $CH_3$, $CH_2CH_3$, Cl, F, Br, —CN, $CF_3$, $NH_2$, $NH(CH_3)$, $N(CH_3)_2$, OH, $OCH_3$, SH, $SCH_3$, and $S(O)_2CH_3$;

$R^2$ is $NR^{6a}R^{7a}$; and, $R^3$ is independently selected at each occurrence from $C_{2-6}$ alkyl substituted with 0–2 $R^a$, $C_{2-6}$ alkenyl substituted with 0–2 $R^a$, $C_{2-6}$ alkynyl substituted with 0–2 $R^a$, $C_{3-6}$ cycloalkyl substituted with 0–2 $R^a$, ($C_{3-6}$ cycloalkyl)$C_{1-2}$ alkyl substituted with 0–2 $R^a$, —$NO_2$, halo, —CN, $C_{1-4}$ haloalkyl, —$NR^6R^7$, —$NR^8COR^{13a}$, —$COR^{13}$, —$OR^{10a}$, —$CONR^6R^7$, —$C(O)OR^{10a}$, and —$S(O)_nR^{12}$.

12. A compound according to claim 11, wherein:

R is phenyl, and is substituted with 1–3 $R^3$ groups;

$R^1$ is selected from H, $CH_3$, $CH_2CH_3$, Cl, and F;

$R^3$ is independently selected at each occurrence from $C_{2-6}$ alkyl substituted with 0–2 $R^a$, $C_{2-6}$ alkenyl substituted with 0–2 $R^a$, $C_{2-6}$ alkynyl substituted with 0–2 $R^a$, $C_{3-6}$ cycloalkyl substituted with 0–2 $R^a$, ($C_{3-6}$ cycloalkyl)$C_{1-2}$ alkyl substituted with 0–2 $R^a$, F, Cl, $C_{1-4}$ haloalkyl, —$NR^6R^7$, —$NR^8COR^{13a}$, —$COR^{13}$, —$OR^{10a}$, —$CONR^6R^7$, —$C(O)OR^{10}$, and —$S(O)_nR^{12}$, $R^a$ is independently selected at each occurrence from $C_{1-4}$ alkyl, —$NO_2$, F, Cl, —CN, —$NR^6R^7$, —$NR^8COR^{13a}$, —$COR^{13}$, —$OR^{10a}$, —$CONR^{6a}R^{7a}$, —$C(O)OR^{10a}$, and —$S(O)_nR^{12}$;

$R^{6a}$ is independently selected at each occurrence from $C_{1-6}$ alkyl substituted with 0–2 $R^b$, $C_{2-6}$ alkenyl substituted with 0–2 $R^b$, $C_{2-6}$ alkynyl substituted with 0–2 $R^b$, $C_{3-6}$ cycloalkyl substituted with 0–2 $R^b$, ($C_{3-6}$ cycloalkyl)$C_{1-4}$ alkyl substituted with 0–2 $R^b$, (aryl)$C_{1-4}$ alkyl substituted with 0–2 $R^b$, (heteroaryl)$C_{1-4}$ alkyl substituted with 0–2 $R^b$, and (heterocyclyl)$C_{1-4}$ alkyl substituted with 0–2 $R^b$;

$R^b$ is independently selected at each occurrence from $C_{1-4}$ alkyl, —$NO_2$, F, Cl, —CN, —$NR^{6b}R^{7a}$, —$NR^8COR^{13a}$, —$COR^{13}$, —$OR^{10a}$, $CONR^{6b}R^{7a}$, —$C(O)OR^{10a}$, and —$S(O)_nR^{12}$; and, $R^{7a}$ is independently selected at each occurrence from H, $C_{1-6}$ alkyl, benzyl, and ($C_{3-6}$ cycloalkyl)methyl.

13. A compound according to claim 12, wherein: $R^1$ is $CH_3$;

$R^3$ is independently selected at each occurrence from $C_{2-6}$ alkyl substituted with 0–2 $R^a$, $C_{2-6}$ alkenyl substituted with 0–2 $R^a$, $C_{2-6}$ alkynyl substituted with 0–2 $R^a$, $C_{3-6}$ cycloalkyl substituted with 0–2 $R^a$, ($C_{3-6}$ cycloalkyl)$C_{1-2}$ alkyl substituted with 0–2 $R^a$, —$NO_2$, halo, —CN, $C_{1-4}$ haloalkyl, —$NR^6R^7$, —$NR^8COR^{13a}$, —$COR^{13}$, $OR^{10a}$, —$CONR^6R^7$, —$C(O)OR^{10a}$, and —$S(O)_nR^{12}$;

$R^a$ is independently selected at each occurrence from $C_{1-4}$ alkyl, —$NO_2$, F, Cl, —CN, —$NR^6R^7$, —$NR^8COR^{13a}$, —$COR^{13}$, —$OR^{10a}$, —$CONR^6R^7$, —$C(O)OR^{10a}$, and —$S(O)_nR^{12}$;

$R^{6a}$ is independently selected at each occurrence from $C_{2-4}$ alkyl substituted with 0–2 $R^b$, ($C_{3-5}$ cycloalkyl)$C_{1-2}$ alkyl substituted with 0–2 groups selected from $CH_3O$ and $CH_3CH_2O$, (aryl)$C_{1-2}$ alkyl substituted with 0–2 $R^b$, (heteroaryl)$C_{1-2}$ alkyl substituted with 0–2 $R^b$, and (heterocyclyl)$C_{1-2}$ alkyl substituted with 0–2 $R^b$;

$R^b$ is independently selected at each occurrence from $C_{1-4}$ alkyl, —$NO_2$, F, Cl, —CN, —$NR^{6b}R^{7a}$, $NR^8COR^{13a}$, —$COR^{13}$, —$OR^{10a}$, —$CONR^{6b}R^{7a}$, —$C(O)OR^{10a}$, and —$S(O)_nR^{12}$;

$R^8$ is independently at each occurrence selected from H, $C_{1-4}$ alkyl, $C_{3-6}$ cycloalkyl and ($C_{3-6}$ cycloalkyl)$C_{1-2}$ alkyl;

$R^9$ is independently at each occurrence selected from H, $C_{1-4}$ alkyl, $C_{3-6}$ cycloalkyl and ($C_{3-6}$ cycloalkyl)$C_{1-2}$ alkyl;

$R^{10}$ is independently at each occurrence selected from H, $C_{1-4}$ alkyl, $C_{1-4}$ haloalkyl, $C_{3-6}$ cycloalkyl, and ($C_{3-6}$ cycloalkyl)$C_{1-2}$ alkyl;

$R^{10a}$ is independently at each occurrence selected from H, $C_{1-6}$ alkyl, phenyl, benzyl, $C_{3-6}$ cycloalkyl, ($C_{3-6}$ cycloalkyl)$C_{1-2}$ alkyl, ($C_{1-4}$ alkoxy)$C_{1-2}$ alkyl, and $C_{1-4}$ haloalkyl;

$R^{10b}$ is independently at each occurrence selected from H, $C_{1-6}$ alkyl, $C_{2-4}$ alkenyl, phenyl, benzyl, $C_{3-6}$ cycloalkyl, ($C_{3-6}$ cycloalkyl)$C_{1-2}$ alkyl, ($C_{1-4}$ alkoxy)$C_{1-2}$ alkyl, and $C_{1-4}$ haloalkyl;

$R^{11}$ is independently at each occurrence selected from $C_{1-4}$ alkyl, $C_{1-4}$ haloalkyl, and $C_{3-6}$ cycloalkyl;

$R^{12}$ is independently at each occurrence selected from $C_{1-4}$ alkyl, $C_{1-4}$ haloalkyl, ($C_{1-4}$ alkoxy)$C_{1-2}$ alkyl, $C_{3-6}$ cycloalkyl, ($C_{3-6}$ cycloalkyl)$C_{1-2}$ alkyl, aryl, and (aryl)$C_{1-2}$ alkyl;

$R^{13a}$ is independently at each occurrence selected from $C_{1-6}$ alkyl, phenyl, benzyl, $C_{3-6}$ cycloalkyl, and ($C_{3-6}$ cycloalkyl)$C_{1-2}$ alkyl;

aryl is independently at each occurrence phenyl substituted with 0–3 $R^g$;

$R^g$ is independently at each occurrence selected from $C_{1-4}$ alkyl, $C_{3-6}$ cycloalkyl, F, Cl, $C_{1-4}$ haloalkyl, cyano, nitro, —$OR^{10a}$, —$S(O)_nR^{15}$, —$COR^{16}$, —$C(O)OR^{16}$, —$NR^8COR^{16a}$, —$NR^{6a}R^{7a}$, and —$CONR^{6a}R^{7a}$;

$R^{15}$ is independently at each occurrence selected from $C_{1-4}$ alkyl, $C_{1-4}$ haloalkyl, ($C_{1-4}$ alkoxy)$C_{1-4}$ alkyl, $C_{3-6}$ cycloalkyl, ($C_{3-6}$ cycloalkyl)$C_{1-2}$ alkyl, phenyl, benzyl, and (phenyl)$C_{1-2}$ alkyl;

$R^{16}$ is independently at each occurrence selected from H, $C_{1-4}$ alkyl, phenyl, benzyl, $C_{3-6}$ cycloalkyl, and $(C_{3-6}$ cycloalkyl$)C_{1-2}$ alkyl;

$R^{16a}$ is independently at each occurrence selected from $C_{1-4}$ alkyl, phenyl, benzyl, $C_{3-6}$ cycloalkyl, and $(C_{3-6}$ cycloalkyl$)C_{1-2}$ alkyl;

heteroaryl is independently at each occurrence selected from pyridyl, pyrimidinyl, furanyl, imidazolyl, thiazolyl, pyrrolyl, oxazolyl, isoxazolyl, pyrazolyl, triazolyl, and tetrazolyl, and is substituted with 0–3 $R^h$;

heterocyclyl is saturated or partially saturated heteroaryl, substituted with 0–3 $R^h$; and, $R^h$ is independently at each occurrence selected from $C_{1-6}$ alkyl, $C_{3-6}$ cycloalkyl, F, Cl, $C_{1-4}$ haloalkyl, cyano, nitro, —$OR^{10a}$, —$S(O)_nR^{15}$, —$COR^{16}$, —$C(O)OR^{16}$, —$NR^8COR^{16a}$, —$NR^{6a}R^{7a}$, and —$CONR^{6a}R^{7a}$.

* * * * *

UNITED STATES PATENT AND TRADEMARK OFFICE
CERTIFICATE OF CORRECTION

PATENT NO.    : 6,294,671 B1                                   Page 1 of 1
DATED         : September 25, 2001
INVENTOR(S)   : William E. Frietze It is certified that error appears in the above-identified patent and that said Letters Patent is hereby corrected as shown below:

Column 12,
Line 34, "incclude" should read -- include --;
Line 45, ""t" should read -- at --;

Column 24,
Line 66, "Re" should read -- $R^e$ --;

Column 26,
Line 36, "—NO2" should read -- —$NO_2$ --;

Column 28,
Line 59, cancel beginning with "3-(2,4-dichlorophenyl)-5-methyl-7-(3-pentoxy)-isoxazolo[4,5-d]pyrimidine" to and including "3-(2,4-dichlorophenyl)-5-methyl-7-(2-methoxy-1-cyclopropylethoxy)-isoxazolo[4,5-d]pyrimidine;" in col. 29, line 4;

Column 29,
Line 66, cancel beginning with "3-(2,4,6-trimethylphenyl)-5-methyl-7-(3-pentoxy)-isoxazolo[4,5-d]pyrimidine" to and including "3-(2,4,6-trimethylphenyl)-5-methyl-7-(2-methoxy-1-cyclopropylethoxy)-isoxazolo[4,5-d]pyrimidine;" in col. 30, line 11; and Column 31,
Line 3, cancel beginning with "3-(2,4-dimethylphenyl)-5-methyl-7-(3-pentoxy)-isoxazolo[4,5-d]pyrimidine" to and including "3-(2,4-dimethylphenyl)-5-methyl-7-(2-methoxy-1-cyclopropylethoxy)isoxazolo[4,5-d]pyrimidine;" in col. 31, line 16.

Signed and Sealed this

Twenty-fourth Day of December, 2002

JAMES E. ROGAN
*Director of the United States Patent and Trademark Office*